United States Patent
Oishi et al.

(10) Patent No.: US 6,977,044 B1
(45) Date of Patent: Dec. 20, 2005

(54) FILTER FOR SELECTIVELY REMOVING LEUKOCYTES

(75) Inventors: Teruhiko Oishi, Oita (JP); Morikazu Miura, Oita (JP); Tatsuya Fukuda, Oita (JP); Hirofumi Miura, Oota-ku (JP)

(73) Assignee: Asahi Medical Co., Ltd., Tokyo (JP)

( * ) Notice: Subject to any disclaimer, the term of this patent is extended or adjusted under 35 U.S.C. 154(b) by 281 days.

(21) Appl. No.: 10/111,989

(22) PCT Filed: Nov. 1, 2000

(86) PCT No.: PCT/JP00/07707

§ 371 (c)(1),
(2), (4) Date: Apr. 30, 2002

(87) PCT Pub. No.: WO01/32236

PCT Pub. Date: May 10, 2001

(30) Foreign Application Priority Data

| Nov. 1, 1999 | (JP) | 11-311474 |
| Feb. 25, 2000 | (JP) | 2000-049729 |
| Mar. 31, 2000 | (JP) | 2000-099715 |

(51) Int. Cl.⁷ ............................................. B01D 39/16
(52) U.S. Cl. ................................................ 210/500.42
(58) Field of Search .................... 210/500.42

(56) References Cited

U.S. PATENT DOCUMENTS 4,936,998 A    6/1990   Nishimura et al.

FOREIGN PATENT DOCUMENTS

| EP | 0 606 646 | 7/1994 |
| JP | A 55-129755 | 10/1980 |
| JP | A 60-119955 | 6/1985 |
| JP | A 60-193468 | 10/1985 |
| JP | 2-46857 | 2/1990 |
| JP | A 2-46857 | 2/1990 |
| JP | 5-262656 | 10/1993 |
| JP | A 5-262656 | 10/1993 |
| JP | 08281100 | * 10/1996 |
| JP | B2 2854857 | 11/1998 |
| JP | 11-206876 | 8/1999 |
| JP | A 11-206876 | 8/1999 |
| JP | 2000-51623 | 2/2000 |
| JP | A 2000-51623 | 2/2000 |
| JP | 2000-197814 | 7/2000 |
| JP | A 2000-197814 | 7/2000 |

* cited by examiner

*Primary Examiner*—Jean C. Witz
(74) *Attorney, Agent, or Firm*—Young & Thompson

(57) ABSTRACT

A filter for selectively removing leukocytes from the human whole blood, characterized in that it comprises a filter base coated with a hydrophilic synthetic polymer having a weight-average molecular weight of 300,000 to 3,000,000 and that the percentage of covering by the polymer is 70% or higher based on the whole surface of the filter base.

14 Claims, 3 Drawing Sheets

FILTER FOR SELECTIVELY REMOVING LEUKOCYTES

BACKGROUND OF THE INVENTION

1. Field of the Invention

The present invention relates to a filter for selectively removing leukocytes. More particularly, the present invention is concerned with a filter for selectively removing leukocytes from human whole blood, which comprises a filter substrate having coated thereon a hydrophilic synthetic polymer in a coating ratio of 70% or more with respect to the overall surface of the filter substrate, wherein the polymer has a specific weight average molecular weight. By the use of the filter of the present invention, it becomes possible to efficiently remove leukocytes (which are causative of various side effects of a transfusion) from human whole blood while holding down a loss of plasma, red cells and platelets. Therefore, the filter of the present invention is extremely useful for the production of blood products. The present invention is also concerned with a method for selectively removing leukocytes from human whole blood, using the above-mentioned filter.

2. Prior Art

At present, the conventional whole blood transfusion has come to be replaced by the blood component transfusion wherein only a blood component necessary for treating a particular disease of the patient is transfused while suppressing the transfusion of an unnecessary blood component to a minimum.

Examples of blood component transfusions include red cell transfusion, platelet transfusion, plasma transfusion and the like. In many cases of the red cell transfusion (which is performed on a patient who needs supplementation of red cells), a red cell concentrate is administered. In many cases of the platelet transfusion (which is performed on a patient who needs supplementation of platelets), a platelet concentrate is administered.

As a problem accompanying the transfusion, there can be mentioned side effects of a transfusion. The blood component transfusion is considered to be one of the measures effective for avoiding the side effects of a transfusion. However, it is known that various side effects are caused even by a blood component transfusion. For example, it has been reported that in a patient who has received a transfusion of a platelet concentrate, a wide variety of side effects may occur, such as non-hemolytic feverish reaction, alloimmune reaction, post-transfusion acute lung injury, graft versus host disease (GVHD), allergic reaction, anaphylactic reaction, viral and bacterial infections and immunosuppression.

It is considered that most of these side effects of a transfusion are caused by leukocytes contained in the blood products employed. Therefore, leukocytes contained in a blood product should be removed so that the number of the leukocytes in the blood product is lowered to a level which does not cause side effects of a transfusion.

Examples of methods for removing leukocytes from a leukocyte-containing cell suspension (such as blood) include:
- a centrifugation method in which a cell suspension is subjected to centrifugation to thereby separate and remove leukocytes;
- a filtration method in which a cell suspension is subjected to filtration to thereby cause the leukocytes contained in the cell suspension to be adsorbed on the filter; and
- a dextran method in which a dextran-containing physiological saline is added to and mixed with a cell suspension placed in a blood bag to obtain a mixture having a floating leukocyte layer, and the leukocyte layer is removed by suction.

Of these methods for removing leukocytes, the filtration method is widely employed due to its advantages that the ability to remove leukocytes is high, the operation is easy and the cost is low.

Various reports have been made with respect to a filter for removing leukocytes. For example, Japanese Patent Application Laid-Open Specification No. 60-193468 discloses a filter for removing leukocytes, which exhibits high efficiency in the removal of leukocytes and can treat blood at an increased rate. This filter comprises a filter material which is a non-woven fabric having a specific fiber diameter and a specific bulk density. However, although this filter is excellent in the leukocyte removal efficiency, the platelet passage ratio of this filter is not satisfactory.

For solving such problem, various studies have conventionally been made in which a coating is formed on a filter substrate in an attempt to simultaneously improve both the leukocyte removal efficiency and the platelet passage ratio with respect to a leukocyte removing filter. However, in any of these studies, it was found that at least one of the leukocyte removal efficiency and the platelet passage ratio is not satisfactory.

For example, Japanese Patent Application Laid-Open Specification No. 55-129755 discloses a method for collecting leukocytes and lymphocytes in a form containing only a small amount of red cells and platelets, wherein the method uses a filter which comprises a filter material which is a non-woven fabric comprising fibers coated with an anti-thrombogenic material, such as a polyether urethane, poly(hydroxyethyl methacrylate) or silicone. However, this filter has a problem in that the leukocyte removal ratio is low.

Japanese Patent Application Laid-Open Specification No. 60-119955 discloses that platelets are extremely unlikely to be adsorbed on a polymer containing a nitrogen-containing basic functional group and having a nitrogen content of from 0.05 to 3.5% by weight. However, this patent document has no disclosure with respect to the affinity of leukocytes to the above-mentioned polymer (i.e., adsorbability of leukocytes on the above-mentioned polymer).

Examined Japanese Patent Application Publication No. 6-51060 (corresponding to U.S. Pat. No. 4,936,998) describes that, with respect to a fiber which contains, in a peripheral surface portion thereof, a nonionic hydrophilic group and a nitrogen-containing basic functional group, platelets are unlikely to be adsorbed on the fiber, whereas leukocytes are likely to be adsorbed on the fiber. This patent document discloses a filter for removing leukocytes, which comprises a filter material which is a non-woven fabric comprising the above-mentioned fiber. Further, this patent document describes that when the above-mentioned filter is used for the treatment of bovine blood, the above-mentioned filter exhibits excellent leukocyte removal efficiency and high platelet passage ratio. However, although this filter exhibits excellent removal efficiency for human leukocytes, this filter is unsatisfactory in the passage ratio of human platelets. In this connection, it should be noted that the low platelet passage ratio of this filter has not been particularly considered as being a problem. The reason for this is that, when this filter is used for the treatment of a platelet concentrate (having high platelet content), still a great amount of platelets can be passed through this filter, so that the platelet passage ratio of this filter is acceptable. On the other hand, however, in the case of the use of this filter for the treatment of human whole blood (having a platelet content lower than that of a platelet concentrate), the platelet passage ratio of this filter is not acceptable.

Japanese Patent No. 2854857 discloses a filter for removing leukocytes, comprising, as a filter material, a non-woven fabric of polyethylene terephthalate, which is coated with chitosan or a derivative thereof. However, when this filter is used for the treatment of human whole blood, although this filter exhibits high platelet passage ratio and high red cell passage ratio, the leukocyte removal efficiency of this filter is extremely low. That is, the leukocyte removing performance of this filter is not satisfactory.

In the production of the conventional filters for removing leukocytes (such as those filters mentioned above), a coating solution having dissolved therein a relatively small amount of a coating material is used, so that the amount of the coating material which covers the surface of the filter substrate of the filter is relatively small. The reasons why a coating solution containing a relatively small amount of a coating material is conventionally used are explained below.

The reason 1 is as follows. A coating material used for producing a leukocyte removing filter is relatively expensive. Therefore, the use of an increased amount of a coating material leads to an increase in the production cost of the filter.

The reason 2 is as follows. When the concentration of a coating material contained in the coating solution is high, the viscosity of the coating solution becomes high, so that uniform coating of the filter substrate with the coating solution becomes difficult.

The reason 3 is as follows. When a hydrophilic polymer is used as a coating material and when the amount of the hydrophilic polymer used is large, it is considered that some water-soluble component will be dissolved-out from the coating material and enter a cell suspension (which has been treated with the filter). It is possible that when the cell suspension containing the water-soluble component is administered to a human body, the water-soluble component exhibits a toxicity.

Further, the above-mentioned Japanese Patent No. 2854857 describes that when a coating solution having a high concentration of a coating material is used, the leukocyte removal ratio of the resultant filter tends to be lowered.

For these reasons, as mentioned above, the amount of the coating material used for producing the conventional filters is relatively small. Therefore, it is considered that in the conventional leukocyte removing filters, a considerably large portion of the surface of the filter substrate remains uncoated. However, the relationship between the coating ratio of the surface of the filter substrate and the performance (i.e., the leukocyte removal efficiency and the platelet passage ratio) of the filter is conventionally not known at all.

SUMMARY OF THE INVENTION

In this situation, the present inventors have made extensive and intensive studies with a view toward developing a filter for removing leukocytes, which exhibits not only high leukocyte removal efficiency but also high platelet passage ratio, and which is applicable to the treatment of human whole blood.

As a result, it has unexpectedly been found that when the surface of the filter substrate of the filter is coated with a hydrophilic synthetic polymer having a specific weight average molecular weight so as to achieve a coating ratio of 70% or more with respect to the overall surface of the filter substrate, there can be obtained a leukocyte removing filter which exhibits not only high leukocyte removal efficiency but also high platelet passage ratio and which is applicable to the treatment of human whole blood.

Further, the present inventors have found that by using, as a coating polymer, a hydrophilic synthetic polymer having a specific molecular weight distribution, the below-mentioned problems accompanying the prior art can be prevented: the dissolution-out of a water-soluble component and a lowering of the leukocyte removal ratio.

The present invention has been completed, based on these novel findings.

Accordingly, it is an object of the present invention to provide a filter for removing leukocytes, which exhibits not only high leukocyte removal efficiency but also high platelet passage ratio and which is applicable to the treatment of human whole blood.

It is another object of the present invention to provide a method for removing leukocytes from human whole blood, using the above-mentioned filter.

The foregoing and other objects, features and advantages of the present invention will be apparent from the following detailed description and appended claims taken in connection with the accompanying drawings.

DESCRIPTION OF REFERENCE NUMERALS

Figure 1:
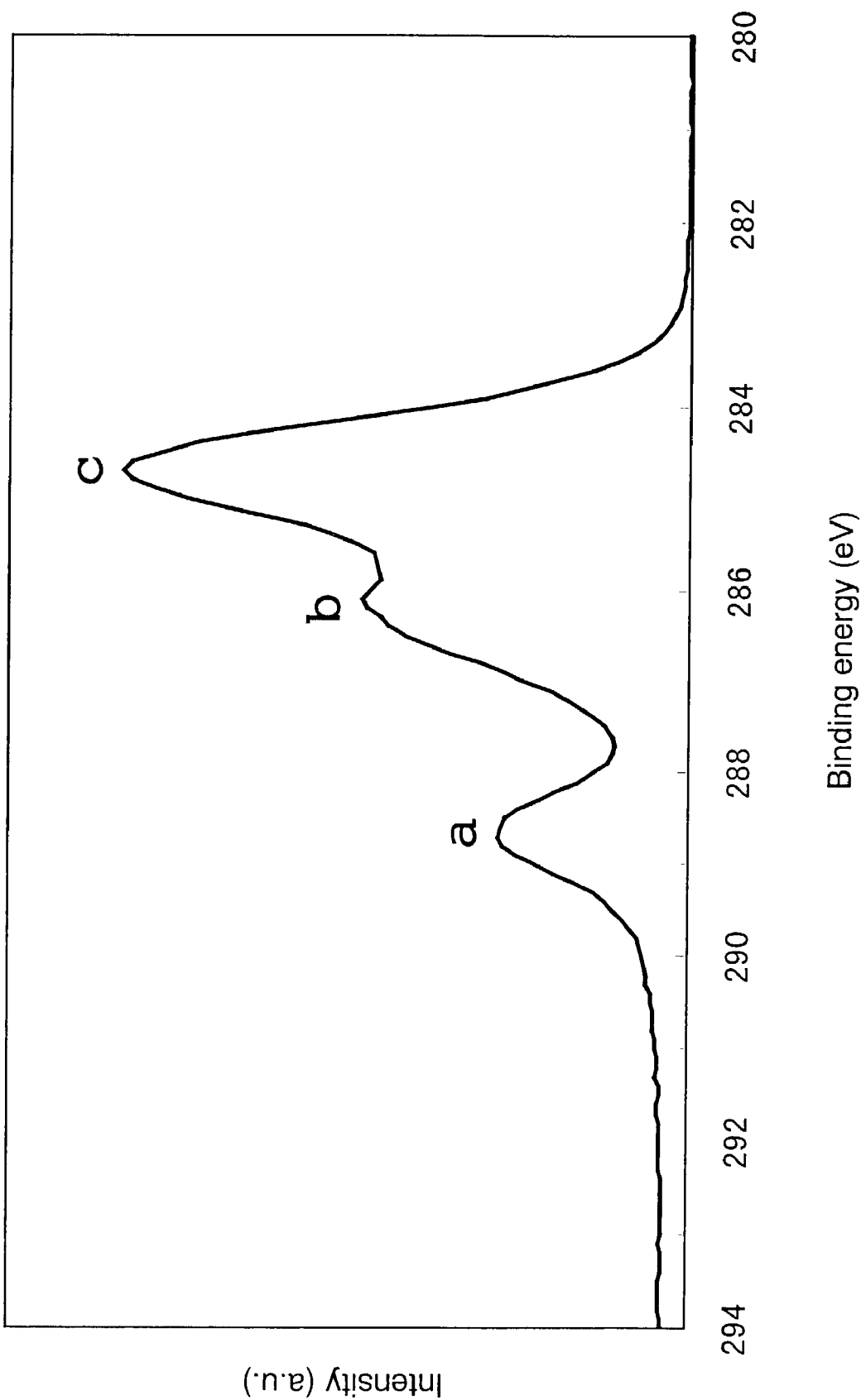
FIG. 1 is an example of an X-ray photoelectron spectrum (XPS) of the filter of the present invention for selectively removing leukocytes.
Figure 2:
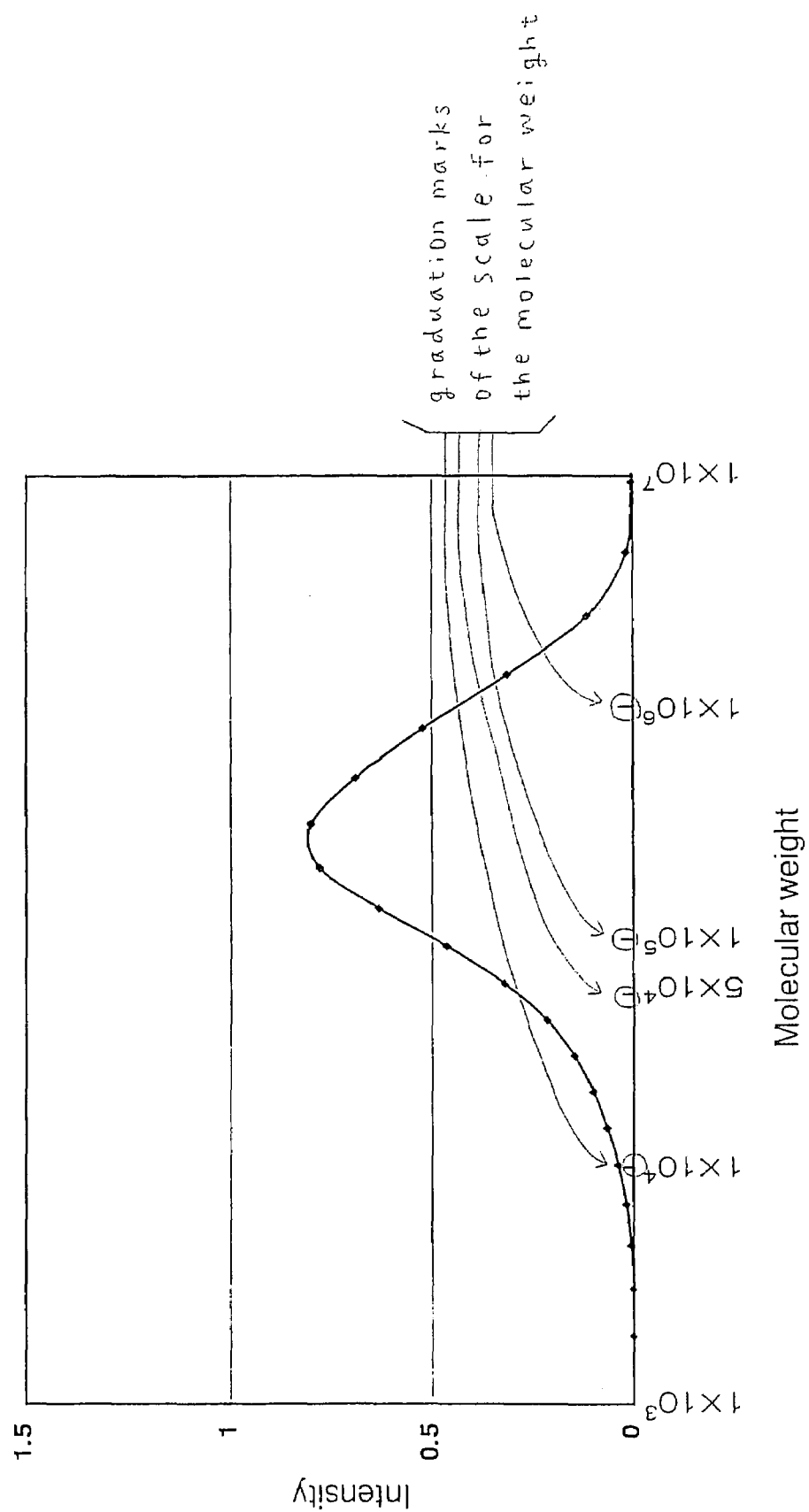
FIG. 2 is a graph showing the molecular weight distribution of the hydrophilic synthetic polymer used for producing the filter of the present invention for selectively removing leukocytes.

1: Roll for supplying a filter substrate
2: Vessel of a polymer solution used for coating
3: Constant temperature vessel for keeping a polymer solution warm
4: Roll
5: Rolls for nipping
6: Suction (suction apparatus for removing an excess polymer solution remaining on the filter substrate)
7: Manometer
8: Trapping apparatus for an excess polymer solution removed from the filter substrate
9: Wind-up roll for a filter
10: Filter substrate
11: Polymer solution
12: Roll for impregnation
13: Pressure controller
14: Water for temperature control of the constant temperature vessel

DETAILED DESCRIPTION OF THE INVENTION

In one aspect of the present invention, there is provided a filter for selectively removing leukocytes from human whole blood, comprising a filter substrate having coated thereon a hydrophilic synthetic polymer in a coating ratio of 70% or more with respect to the overall surface of the filter substrate, the polymer having a weight average molecular weight of from 300,000 to 3,000,000.

For easy understanding of the present invention, the essential features and various preferred embodiments of the present invention are enumerated below.
1. A filter for selectively removing leukocytes from human whole blood, comprising a filter substrate having coated thereon a hydrophilic synthetic polymer in a coating ratio of 70% or more with respect to the overall surface of the filter substrate, the polymer having a weight average molecular weight of from 300,000 to 3,000,000.
2. The filter according to item 1 above, wherein the hydrophilic synthetic polymer is a vinyl polymer.
3. The filter according to item 1 or 2 above, wherein the hydrophilic synthetic polymer contains a nonionic hydrophilic group and a nitrogen-containing basic functional group.
4. The filter according to any one of items 1 to 3 above, wherein the filter substrate comprises a polymer containing a functional group having a lone electron pair.
5. The filter according to any one of items 1 to 4 above, wherein the filter substrate comprises a thermoplastic polymer.
6. The filter according to any one of items 1 to 5 above, wherein the filter substrate is a non-woven fabric.
7. The filter according to any one of items 1 to 6 above, wherein the filter substrate has been subjected to at least one treatment selected from the group consisting of energy beam irradiation treatment and electric discharge treatment.
8. The filter according to any one of items 1 to 7 above, wherein the hydrophilic synthetic polymer has a molecular weight distribution wherein, in a gel permeation chromatogram of the polymer, the content of low molecular weight fractions having molecular weights which are ¼ or less of the peak-top molecular weight is 10% or less in terms of the percentage of an area in the peak which corresponds to the low molecular weight fractions, based on the entire area of the peak.
9. A method for selectively removing leukocytes from human whole blood, comprising:
   contacting human whole blood with the filter of any one of items 1 to 8 above, thereby causing leukocytes contained in the human whole blood to selectively adhere to the filter while allowing plasma, red cells and platelets contained in the human whole blood to pass through the filter to obtain a leukocyte-removed blood suspension, and
   collecting the leukocyte-removed blood suspension.

Hereinbelow, the present invention is described in detail.

The filter of the present invention for selectively removing leukocytes from human whole blood comprises a filter substrate having coated thereon a hydrophilic synthetic polymer in a coating ratio of 70% or more with respect to the overall surface of the filter substrate. As explained below in detail, the above-mentioned coating ratio (%) is obtained from the amount of the hydrophilic synthetic polymer present in the coated portion of the surface of the filter substrate and the amount of the filter substrate present in the non-coated portion of the surface of the filter substrate, wherein each amount is measured by X-ray photoelectron spectroscopy.

In the present invention, as a polymer for coating the surface of the filter substrate, a hydrophilic synthetic polymer is used. The hydrophilic synthetic polymer has a weight average molecular weight of from 300,000 to 3,000,000, preferably from 300,000 to 2,000,000, more preferably from 350,000 to 2,000,000. When the weight average molecular weight is less than 300,000, the platelet passage ratio of the filter tends to be lowered. On the other hand, when the weight average molecular weight is more than 3,000,000, the hydrophilic synthetic polymer tends to be insoluble in a solvent, so that the coating becomes difficult.

A hydrophilic synthetic polymer is excellent in that the structure and molecular weight thereof can be satisfactorily controlled. Further, the amount of impurities contained in the hydrophilic synthetic polymer is small.

Among the hydrophilic synthetic polymers, a hydrophilic synthetic polymer obtained by polycondensation is disadvantageous in that it has a relatively low molecular weight, i.e., approximately several tens of thousands or less. Generally, the lower the molecular weight of a hydrophilic synthetic polymer, the more the amount of water-soluble impurities contained therein and, hence, the higher the probability that the above-mentioned problem due to the dissolution-out of a water-soluble component occurs.

On the other hand, a hydrophilic natural polymer (such as cellulose, chitin and chitosan) is excellent in that it has a high molecular weight and that the content of impurities (including water-soluble impurities) is low. However, it is difficult to stably provide a hydrophilic natural polymer having a specific molecular weight.

With respect to the hydrophilic synthetic polymer used in the present invention, there is no particular limitation, as long as the polymer can be swelled with water but is insoluble in water. As an example of such a hydrophilic synthetic polymer, there can be mentioned a polymer having at least one substituent, such as a sulfonic acid group, a carboxyl group, a carbonyl group, an amino group, an amido group, a cyano group, a hydroxyl group, a methoxy group, a phosphoric acid group, a polyoxyethylene group comprising 1 to 40 recurring unit(s), an imino group, an imido group, an iminoether group, a pyridyl group, a pyrrolidonyl group, an imidazolyl group and a quaternary ammonium group. These substituents can be used individually or in combination.

In the present invention, it is preferred that the hydrophilic synthetic polymer is a vinyl polymer. In the present invention, the term "vinyl polymer" is intended to mean a vinyl polymer taken in a broad sense, i.e., a polymer in which the main chain comprises acyclic carbon atoms. As specific examples of vinyl polymers, there can be mentioned a poly(acrylic acid) and derivatives thereof; a polymer of an α-substituted acrylic acid and derivatives thereof; a poly (vinyl ether); a poly(vinyl alcohol); a poly(vinyl ester); a polystyrene and derivatives thereof; and a copolymer containing at least one monomer unit of the above-mentioned polymers, wherein these vinyl polymers are described in "Polymer Handbook, Third Edition", pp. VII-5 to VIII-18 (written by J. Brandrup and E. H. Immergut, published by A Willey-Interscience Publication, U.S.A., 1989).

The use of a vinyl polymer is advantageous for the following reason. Even if the vinyl polymer has a high molecular weight, the viscosity of a solution of the vinyl polymer is extremely low, as compared to the case of a natural polymer having the same molecular weight as that of the vinyl polymer. Therefore, a vinyl polymer is easy to handle, and the coating of the filter substrate with a vinyl polymer can be easily performed.

Among vinyl polymers, a copolymer containing a nonionic hydrophilic group and a nitrogen-containing basic functional group is preferred since the adsorbability of platelets on such a copolymer is low. Such a copolymer can be obtained by copolymerizing a vinyl monomer having a nonionic hydrophilic group with a vinyl monomer having a nitrogen-containing basic functional group.

Examples of nonionic hydrophilic groups include a hydroxyl group, an amido group and a polyoxyethylene group comprising 1 to 40 recurring unit(s).

Examples of vinyl monomers having a nonionic hydrophilic group include 2-hydroxyethyl(meth)acrylate, 2-hydroxypropyl(meth)acrylate, vinyl alcohol (a polymer of this vinyl monomer, i.e., poly(vinyl alcohol) can be obtained by a method in which vinyl acetate is polymerized to obtain poly(vinyl acetate), and the obtained poly(vinyl acetate) is subjected to hydrolysis), (meth)acrylamide, N-vinylpyrrolidone and an alkoxypolyethylene glycol (meth)acrylate (such as methoxyethylene glycol (meth)acrylate, methoxydiethylene glycol (meth)acrylate, methoxytriethylene glycol (meth) acrylate or methoxytetraethylene glycol (meth)acrylate). Among these vinyl monomers, from the viewpoint of availability, handling in polymerization and the blood filtration performance of the filter obtained, 2-hydroxyethyl acrylate and 2-hydroxyethyl methacrylate are preferred.

As nitrogen-containing basic functional groups usable in the present invention, there can be mentioned, for example, a primary amino group, a secondary amino group, a tertiary amino group, and a quaternary ammonium group, and nitrogen-containing aromatic ring groups, such as a pyridyl group and an imidazolyl group. Examples of vinyl monomers having these functional groups include allylamine; (meth)acrylic acid derivatives, such as dimethylaminoethyl (meth)acrylate, diethylaminoethyl (meth)acrylate, dimethylaminopropyl (meth)acrylate and 3-dimethylamino-2-hydroxypropyl (meth)acrylate; styrene derivatives, such as p-dimethylaminostyrene and p-dimethylaminoethylstyrene; vinyl derivatives of nitrogen-containing aromatic compounds, such as 2-vinylpyridine, 4-vinylpyridine and 4-vinylimidazole; and derivatives obtained by converting the above-mentioned vinyl compounds to a quaternary ammonium salt by the reaction with an alkyl halide or the like. Among these vinyl polymers, from the viewpoint of availability, handling in polymerization and the blood filtration performance of the filter obtained, dimethylaminoethyl (meth)acrylate and diethylaminoethyl (meth)acrylate are preferred.

In the present invention, with respect to the copolymer containing a nonionic hydrophilic group and a nitrogen-containing basic functional group, it is preferred that the content of basic nitrogen atoms in the copolymer is from 0.05 to 4.0% by weight, more advantageously from 0.2 to 1.5% by weight. When the content of basic nitrogen atoms is less than 0.05% by weight, although the adsorbability of platelets on the copolymer tends to become low, the adsorbability of leukocytes on the copolymer also tends to become low. As a result, it becomes impossible to selectively remove leukocytes. On the other hand, when the content of basic nitrogen atoms is more than 4.0% by weight, both of the adsorbability of platelets on the copolymer and the adsorbability of leukocytes on the copolymer tend to become high. As a result, also in this case, it becomes impossible to selectively remove leukocytes.

In the present invention, with respect to the copolymer containing a nonionic hydrophilic group and a nitrogen-containing basic functional group, it is preferred that the amount of the nonionic hydrophilic groups (in terms of the amount of at least one member selected from the group consisting of a hydroxyl group, an amido group and a polyoxyethylene group) is equimolar or more relative to the amount of basic nitrogen atoms, more advantageously 3 or more times as large as the molar amount of basic nitrogen atoms. The term "basic nitrogen atom" means a nitrogen atom contained in the above-mentioned nitrogen-containing basic functional group.

When the amount of nonionic hydrophilic groups is less than an equimolar amount relative to the amount of basic nitrogen atoms, not only leukocytes but also platelets tend to be removed by adsorption onto the filter.

The amounts of nonionic hydrophilic groups and nitrogen-containing basic functional groups and the amount of basic nitrogen atoms can be determined by a conventional method, such as infrared absorption spectrophotometry (performed by means of a multiple total reflection infrared spectrometer), elemental analysis and nuclear magnetic resonance spectroscopy.

The filter of the present invention for selectively removing leukocytes comprises a filter substrate having coated thereon the above-explained hydrophilic synthetic polymer.

Examples of polymers usable in the present invention as a material for the filter substrate include synthetic polymers, such as an aliphatic polyamide, an aromatic polyamide, a polyester, a poly(meth)acrylate, a poly(methyl(meth)acrylate), a poly(vinyl formal), a poly(vinyl acetal), a polyacrylonitrile, a polysulfone, a polyether sulfone, a polycarbonate, a polyurethane, a polyether imide and a polyimide; natural polymers, such as cellulose and cellulose acetate; cellulose derivatives in which a functional group of cellulose is modified, such as nitrocellulose; and regenerated cellulose. The polymers used in the present invention as a material for the filter substrate are not limited to the above-mentioned examples.

In addition, other polymers also can be used as a material for the filter substrate, as long as a functional group having a lone electron pair can be introduced into the surface of the filter substrate by the below-described energy beam irradiation treatment (such as electron beam irradiation and γ(gamma)-ray irradiation) or electric discharge treatment (such as corona discharge treatment and plasma treatment). Examples of such polymers include polyethylene, polypropylene, poly(4-methylpentene), polystyrene, poly(vinyl chloride), poly(vinyl fluoride), poly(vinylidene fluoride), poly(vinylidene chloride) and polytrifluorochloroethylene.

With respect to the filter of the present invention for selectively removing leukocytes, it is preferred that the filter substrate comprises a polymer containing a functional group having a lone electron pair.

As described below, in the present invention, the filter substrate must be coated with a hydrophilic synthetic polymer in a coating ratio of 70% or more with respect to the overall surface of the filter substrate. For achieving a coating ratio of 70% or more, selection of the material for the filter substrate is extremely important. For increasing the coating ratio, the affinity between the filter substrate and the hydrophilic synthetic polymer is extremely important. When the affinity between the filter substrate and the hydrophilic synthetic polymer is poor, the coating ratio tends not to be increased, even if the amount of the hydrophilic synthetic polymer is increased. For example, a filter substrate composed of a highly hydrophobic material has a poor affinity to the hydrophilic synthetic polymer, which usually has a high surface energy (in other words, the wettability of such filter substrate with the hydrophilic synthetic polymer is poor). As a result, even if a large amount of the hydrophilic synthetic polymer is used, the coating ratio cannot be increased.

However, even in the case of such a filter substrate composed of a highly hydrophobic material, the coating ratio can be increased by a method in which a functional group having a lone electron pair is introduced to the surface of the filter substrate by the below-described energy beam irradiation treatment (such as electron beam irradiation and γ(gamma)-ray irradiation) or electric discharge treatment (such as corona discharge treatment and plasma treatment).

When the number of functional groups each having a lone electron pair in the polymer constituting the filter substrate is increased, the affinity of the filter substrate to the hydrophilic synthetic polymer is improved, so that the coating ratio tends to be increased.

As examples of functional groups having a lone electron pair, which are usable in the present invention, there can be mentioned an ether group, an ester group, a urethane group, a sulfone group, a carbonyl group, an amino group, an amido group, a cyano group, an imino group and an imido group. The functional groups having a lone electron pair are not limited to the above-mentioned examples. It is preferred to use, as a material for the filter substrate, a polymer comprising recurring units each having at least one of these functional groups.

In addition to polymers having the above-mentioned functional group, preferred examples of polymers for constituting the filter substrate also include polymers having a hydrophilic functional group containing a lone electron pair. Examples of hydrophilic functional groups containing a lone electron pair include a sulfonic acid group, a carboxyl group, a hydroxyl group, a phosphoric acid group, an iminoether group, a pyridyl group, a pyrrolidonyl group and an imidazolyl group. Polymers having such a hydrophilic functional group have a drawback in that the polymers are susceptible to swelling with water and hence exhibit a lowering of the mechanical strength. However, as long as such a polymer can maintain a mechanical strength which is sufficient for its use as a substrate of a filter for selectively removing leukocytes, the polymer can be used as a material for the filter substrate.

The form of the filter substrate of the filter of the present invention is not particularly limited, but may be any of a non-woven fabric produced by a melt blow method, a flash spinning method or a wet lay method; a woven fabric; or a porous article in the form of a flat membrane, a tubular membrane, a hollow fiber membrane or the like. A non-woven fabric is especially preferred as the filter substrate. The terminology "non-woven fabric" used herein means a cloth-form fabric in which a mass of fibers or yarns are chemically, thermally or mechanically bonded without weaving. In the present invention, a fibrous filter (such as a woven or non-woven fabric) can be used in combination with a porous article filter, wherein these two types of filers can be accommodated in the same casing for a filter.

When the form of the filter substrate is a non-woven or woven fabric, it is preferred that the filter substrate has an average fiber diameter of from 0.3 to 10 μm, more advantageously from 0.3 to 3 μm, still more advantageously from 0.5 to 1.8 μm. When the average fiber diameter of the filter substrate is less than 0.3 μm, it is possible that the filter cannot be of practical use, because the filter exhibits too large a pressure loss in the filtration of human whole blood or the like. On the other hand, when the average fiber diameter of the filter substrate is more than 10 μm, the probability of contacting between the fibers and leukocytes becomes too low, leading to a lowering of the leukocyte removal efficiency of the filter.

The term "average fiber diameter" used in the present invention means an average diameter of fibers, which is obtained by a method in which, from a non-woven or woven fabric constituting the filter substrate, a portion of the filter substrate is sampled out and a photograph of the sampled filter substrate is taken using an electron microscope, and an average fiber diameter is determined from the photomicrograph. Specifically, the average fiber diameter is obtained by the following procedure.

From a non-woven or woven fabric constituting the filter substrate, a portion of the filter substrate, which is recognized as being substantially uniform, is cut-out as a sample and the resultant sample is photographed using, for example, a scanning electron microscope. In the sampling, the filter substrate is sectioned into 0.5 cm×0.5 cm squares. From them, six squares are randomly sampled. In the random sampling, for example, an address is given to each of the above-mentioned square sections, and appropriate square sections are chosen, for example by a method in which the table of random numbers is used. With respect to each of the first sampled three square sections, the center portion of one surface (hereinafter, for convenience's sake, this surface is referred to as "surface A") is photographed at a magnification of 2500. On the other hand, with respect to each of the remaining three square sections, the center portion of the other surface (hereinafter, for convenience's sake, this surface is referred to as "surface B") is photographed at the same magnification as mentioned above. In the photographing, a plurality of photographs are taken at the center portion and its neighborhood with respect to each of the sampled square sections. Photographing is continued until the number of fibers appearing in the photographs exceeds 100. The diameter is measured of each of the fibers appearing in the photographs. The term "diameter" used herein means the width of a fiber as viewed in a direction perpendicular to the fiber axis. The average fiber diameter is the quotient of the sum of all measured fiber diameters divided by the number of fibers, provided that when a plurality of fibers overlap each other to cause the measurement of the fiber width to be infeasible due to the shadowing of other fibers, or when a plurality of fibers are formed into a thick mass of fiber by melt adhesion or the like, or when fibers of markedly different diameters are mixed, measured data are omitted. Further, when the average fiber diameters are clearly different between surface A and surface B of the filter substrate, it is not regarded as a single filter substrate. The expression "average fiber diameters are clearly different" used herein means that a statistically significant difference exists between average fiber diameters. In the case where such a statistically significant difference exists, surface A and surface B are regarded as constituting different filter substrates. A boundary is determined between surface A and surface B, and subsequently the average fiber diameters are separately measured for surfaces A and B. Surfaces A and B are separately evaluated with respect to average fiber diameter.

With respect to the filter substrate comprising a non-woven or woven fabric, it is preferred that the porosity of the filter substrate is from 50% to less than 95%, more advantageously from 70% to less than 90%. When the porosity is less than 50%, the flow of a liquid (such as blood) containing leukocytes and/or platelets through the filter becomes stagnant. On the other hand, when the porosity is 95% or more, the mechanical strength of the filter is lowered.

The porosity of the filter substrate is measured as follows. From the filter substrate is cut off a segment having a predetermined area, and the dry weight (W1) and thickness of the segment are measured. Further, the volume (V) of the segment is calculated from the area and thickness of the segment. Then, the segment is immersed in purified water, and subjected to degassing for removing air from the pores of the segment, to thereby impregnate the segment with water. The weight (W2) of the obtained water-impregnated segment is measured. From the thus obtained values V, W1 and W2, the porosity of the filter substrate is calculated in accordance with following formula:

$$\text{Porosity (\%)} = \frac{W2 - W1}{\rho} \times \frac{1}{V} \times 100$$

wherein ρ represents the specific gravity of the purified water.

In the present invention, when a porous article is used to prepare the filter substrate, the average pore diameter of the porous article is generally from 1 to 60 μm, preferably from 1 to 30 μm, more preferably from 1 to 20 μm. When the average pore diameter is less than 1 μm, the flow of a liquid (such as blood) containing leukocytes and/or platelets through the filter becomes stagnant. On the other hand, when the average pore diameter is more than 60 μm, the probability of contacting between the filter substrate and leukocytes becomes too low, leading to a lowering of the leukocyte removal efficiency of the filter. In the present invention, the average pore diameter is determined by the air flow method described in ASTM F316-86, using POROFIL liquid (manufactured and sold by COULTER ELECTRONICS LTD., England).

In the present invention, hereinafter, a component constituting the matrix of the filter substrate is referred to as a "filter substrate element". For example, when the filter substrate is composed of a non-woven or woven fabric, the fibers of the non-woven or woven fabric are the "filter substrate element". When the filter substrate is composed of a porous article, the matrix constituting the porous article, which has a continuous, three-dimensional network structure, is the "filter substrate element".

In the present invention, it is preferred to use a filter substrate produced by any of the following techniques: wet shaping (wet spinning) in accordance with the nonsolvent induced phase separation method; hot-melt shaping (hot-melt spinning) in accordance with the thermally induced phase separation method; and conventional hot-melt shaping (hot-melt spinning) used for producing fibers.

However, in the wet shaping for producing the filter substrate, it is necessary to use not only a solvent for a raw material for the filter substrate but also a non-solvent for the raw material. Therefore, disadvantages are likely to be caused that the solvent and/or non-solvent remain(s) in the ultimate filter and is eluted into blood, and that specific cells are adsorbed on the filter. Therefore, in the present invention, it is preferred to use a filter substrate produced by hot-melt shaping.

With respect to the details of the wet shaping (wet spinning) in accordance with the nonsolvent induced phase separation method, reference can be made to "Maku Gijutsu (Membrane technology)", second edition, pp. 59–123 (co-authored by Masakazu Yoshikawa, Tsuyoshi Matsuura and Tsutomu Nakagawa, published by IPC Inc., Japan (1997)).

With respect to the details of the hot-melt shaping (hot-melt spinning) in accordance with the thermally induced phase separation method, reference can be made to "Netsuyuukibunri hou (TIPS hou) ni yoru koubunsikei takousitsumaku no sakusei (Production of a porous polymer membrane by thermally induced phase separation (TIPS) method)" written by Hideto Matsuyama ("Chemical Engineering", June 1998, pp. 45–56, published by Kagaku Kogyosha Inc., Japan).

In the production of the filter substrate by hot-melt shaping (hot-melt spinning), it is necessary to use a thermoplastic polymer as a material for the filter substrate.

Examples of thermoplastic polymers include polyamide, polyester, polyacrylonitrile, polytrifluorochloroethylene, polystyrene, poly(methyl(meth)acrylate), polyethylene, polypropylene, poly(4-methylpentene), cellulose, cellulose acetate, polysulfone, polyether imide, poly(meth)acrylate, polyvinylidene fluoride, polyimide and polyurethane. The thermoplastic polymers used in the present invention are not limited to those exemplified above. Among the above-exemplified thermoplastic polymers, polytrifluorochloroethylene, polyethylene, polypropylene, poly(4-methylpentene) and polyvinylidene fluoride do not have the above-mentioned functional group having a lone electron pair. However, a filter substrate produced from any of these polymers can be used in the present invention by subjecting such a filter substrate (prior to coating with the hydrophilic synthetic polymer) to an appropriate pretreatment, such as an energy beam irradiation and an electrical discharge treatment. By such a pretreatment, a functional group having a lone electron pair (such as a ketone group and hydroxyl group) can be effectively and easily introduced into the surface of the filter substrate (and/or the surface of the filter substrate element) in an amount sufficient for improving the coating ratio.

With respect to the filter substrate produced from a polymer containing a functional group having a lone electron pair, by subjecting the filter substrate (prior to coating with the hydrophilic synthetic polymer) to the above-mentioned pretreatment, the coating ratio can be further improved.

Examples of energy beam irradiation methods include ultraviolet light irradiation and irradiation of radio active rays, such as electron beam and γ-ray. All of these energy beam irradiation methods are effective for improving the coating ratio. However, for improving the coating ratio without causing degradation of the filter substrate (i.e., without causing damage to the filter substrate), the electron beam irradiation is preferred.

It is preferred that the electron beam irradiation is performed under conditions wherein the absorbed dose is from 10 to 1,000 kGy (kilogray), more advantageously from 10 to 300 kGy. When the absorbed dose is less than 10 kGy, the amount of the functional group having a lone electron pair (introduced into the surface of the filter substrate by the irradiation) is not sufficient for improving the coating ratio. On the other hand, when the absorbed dose is more than 1,000 kGy, the mechanical strength of the filter substrate is disadvantageously lowered.

The electrical discharge treatment is roughly classified into a plasma treatment and a corona discharge treatment. Both of these treatments are effective for improving the coating ratio. However, the corona discharge treatment can be performed using a simple apparatus as compared to the case of the plasma treatment.

The conditions for the corona discharge treatment are defined and optimized in terms of the discharge amount and the discharge intensity.

It is preferred that the discharge amount is from 10 to 3,000 W/(m²/minute), more advantageously from 50 to 3,000 W/(m²/minute), still more advantageously from 50 to 500 W/(m²/minute). In the present invention, the term "discharge amount" is intended to mean a value obtained by dividing the electric energy (W) used for corona discharge treatment by the product of the corona discharge treatment rate (m/minute) (i.e., the length of the filter substrate treated per minute) multiplied by the length (m) of the electrode. When the discharge amount is less than 10 W/(m²/minute), the amount of the functional group having a lone electron pair (introduced into the surface of the filter substrate by the irradiation) is not sufficient for improving the coating ratio. On the other hand, when the discharge amount is more than 3,000 W/(m²/minute), the filter substrate tends to suffer marked oxidative deterioration and becomes difficult to use.

In the present invention, the discharge intensity as well as the discharge amount is extremely important in the corona discharge treatment. It is preferred that the discharge intensity is from 1 to 1,000 W/cm², more advantageously from 10 to 500 W/cm². The term "discharge intensity" is a value indicating the intensity of corona radiated from the electrode, which corresponds to the electric energy (W) supplied to the electrode per unit area (cm²) of the electrode.

The higher the discharge intensity, the higher the productivity of the filter. However, when the discharge intensity is more than 1,000 W/cm², the filter substrate tends to suffer marked oxidative deterioration. On the other hand, when the discharge intensity is less than 1 W/cm², the productivity of the filter tends to be lowered.

In addition to the above-mentioned two conditions, the voltage for the treatment and the distance between the electrode and the filter substrate are also important in the corona discharge treatment.

It is preferred that the voltage for the treatment is from 1 to 100 kV (kilovolt), more advantageously from 5 to 100 kV, still more advantageously from 5 to 50 kV. When the voltage is less than 1 kV, the intensity of corona is not satisfactory. On the other hand, when the voltage is more than 100 kV, the filter substrate tends to suffer marked oxidative deterioration.

With respect to the distance between the electrode and filter substrate, there is no particular limitation, as long as the coating ratio can be effectively improved. It is preferred that the distance between the electrode and filter substrate is from 0.1 to 10 mm, more advantageously from 0.5 to 10 mm, still more advantageously from 0.5 to 5 mm. When the distance is less than 0.1 mm, the filter substrate may come into contact with the electrode. On the other hand, when the distance is more than 10 mm, the coating ratio is not improved.

In many cases, the surface of the filter substrate (and/or the surface of the filter substrate element) after the energy beam irradiation or the electrical discharge treatment has some residual electric charge. In such a filter substrate, an excessive amount of the hydrophilic synthetic polymer may be adhered to a portion having a residual electric charge, so that unevenness of coating or adhesion may occur. Therefore, for preventing such unevenness, it is preferred that, prior to coating, the filter substrate after the energy beam irradiation or electrical discharge treatment is subjected to destaticization by means of a static eliminator.

In the filter of the present invention, the filter substrate which is coated with the hydrophilic synthetic polymer has a coating ratio of 70% or more with respect to the overall surface of the filter substrate. The coating ratio (%) is determined from the amount of the hydrophilic synthetic polymer present in the coated portion of the surface of the filter substrate and the amount of the filter substrate present in the non-coated portion of the surface of the filter substrate, wherein each amount is individually measured by X-ray photoelectron spectroscopy (XPS).

In the present invention, the term "coating ratio" means the proportion of the surface (of the filter substrate) which is coated with the hydrophilic synthetic polymer to the total surface of the elements constituting the filter substrate. At present, there is no means to accurately determine the coating ratio of the overall surface of the filter substrate. Therefore, in the present invention, both surfaces of a filter are analyzed by XPS to determine the coating ratio of both surfaces, and the determined value of coating ratio is taken as representing the coating ratio of the filter substrate. The filter substrate in the present invention has coated thereon a hydrophilic synthetic polymer in a coating ratio of 70% or more, more preferably 90% or more with respect to the overall surface of the filter substrate. This feature is most important in the present invention and essential for attaining the object of the present invention, that is, "to provide a filter for selectively removing leukocytes, which exhibits not only high leukocyte removal efficiency but also high platelet passage ratio and which is advantageously applicable to the treatment of human whole blood." When the coating ratio is less than 70%, the filter is likely to suffer either a drastic lowering of the platelet passage ratio or a wide variance in the platelet passage ratio.

Further, in the present invention, the higher the coating ratio, the higher the platelet passage ratio. Therefore, in the present invention, it is preferred that the coating ratio is as high as possible. It is ideal to prepare a filter substrate having a coating ratio of 100%, but it is very difficult to obtain a coating ratio of 100% unless the affinity between the hydrophilic synthetic polymer and the filter substrate is extremely high.

The reason for the close relationship between the coating ratio and the performance of the filter, especially the platelet passage ratio, has not yet been elucidated. However, the reason is presumed to be as follows.

The surface of the filter substrate has a number of portions where the platelet adsorption is likely to occur (hereinafter, such portions are referred to as "platelet adsorption sites"). Therefore, when a filter substrate which has its surface exposed is contacted with platelets, the platelets are adsorbed on the filter substrate.

By coating the surface of the filter substrate with a hydrophilic synthetic polymer to thereby cover the platelet adsorption sites of the filter substrate, the platelets can be prevented from being adsorbed on the filter substrate and therefore the platelet passage ratio can be increased.

Accordingly, the factor which is closely related to the platelet passage ratio is the proportion of the surface (of the filter substrate) which is coated with the hydrophilic synthetic polymer, namely the coating ratio, but not the amount of the hydrophilic synthetic polymer coated on the filter substrate.

As mentioned above, in the production of the conventional filters for removing leukocytes, a coating solution having dissolved therein a relatively small amount of a coating material is used, so that the amount of the coating material which covers the surface of the filter substrate of the filter is relatively small. Some reasons why a coating solution containing a relatively small amount of a coating material is conventionally used are explained again below.

The reason 1 is as follows. A coating material used for producing a leukocyte removing filter is relatively expensive. Therefore, the use of an increased amount of a coating material leads to an increase in the production cost of the filter.

The reason 2 is as follows. When the concentration of a coating material contained in the coating solution is high, the viscosity of the coating solution becomes high, so that uniform coating of the filter substrate with the coating solution becomes difficult.

Further, it is conventionally known that, when the amount of a hydrophilic polymer used for coating a filter substrate, the leukocyte removal ratio of the resultant filter tends to be lowered. Therefore, it has been considered that, when the filter substrate is coated with a large amount of a hydrophilic polymer, the leukocyte removing performance of the resultant filter cannot be satisfactory.

For these reasons, as mentioned above, the amount of the coating material used for producing the conventional filters is relatively small. Therefore, it is considered that in the conventional leukocyte removing filters, a considerably large portion of the surface of the filter substrate remains uncoated.

For example, in Example 1 and Comparative Example 2 of the present specification, a non-woven fabric of polyethylene terephthalate fiber is coated with a copolymer of 2-hydroxyethyl methacrylate with dimethylaminoethyl methacrylate, and it is shown that when the coating solution used has a copolymer concentration of 8.15% by weight, the coating ratio is 90% (Example 1) and that when the coating solution used has a copolymer concentration of 0.25% by weight, the coating ratio is 40% (Comparative Example 2).

In the Working Examples of the above-mentioned Examined Japanese Patent Application Publication No. 6-51060 (corresponding to U.S. Pat. No. 4,936,998), a non-woven fabric of polyethylene terephthalate fiber is coated with a copolymer of 2-hydroxyethyl methacrylate with dimethylaminoethyl methacrylate, wherein the coating solution used has a copolymer concentration of 0.1%. Since the types of the filter substrate and hydrophilic polymer used in this patent document are the same as those used in the present invention, it is considered that the coating ratio of the filter substrate used in this patent document is less than 40%.

The coating ratio of the filter substrate of the leukocyte removing filter of the present invention is determined by X-ray photoelectron spectroscopy (hereinafter referred to as "XPS"), which is a method in which a monochromatic X-ray source is used to measure the chemical state of an object at its portion from the surface to a depth of, generally, several tens to 100 angstroms (Å). Specifically, the coating ratio can be determined as follows.

First, an element or a partial molecular structure is preselected which most clearly reflects, in an XPS spectrum, the amounts of the filter substrate and hydrophilic synthetic polymer present in the surface of the filter. Such an element or partial molecular structure can be preselected based on the differences in structure between the filter substrate and the hydrophilic synthetic polymer. Specifically, for example, a suitable element or partial molecular structure can be preselected based on the following differences:
  a difference that a specific element is contained in the filter substrate, but not contained in the hydrophilic synthetic polymer; and
  a difference that a specific partial molecular structure is common to both the filter substrate and the hydrophilic synthetic polymer, but the amount of the specific partial molecular structure is different between the filter substrate and the hydrophilic synthetic polymer.

Next, with respect to each of a sample of the filter substrate and a sample of the hydrophilic synthetic polymer, an XPS spectrum is obtained. In each of the obtained XPS spectra, the ratio of the area of the peak ascribed to the preselected element or partial molecular structure to the area of a different peak which has been preselected as a standard is obtained, and the peak area ratios which have been obtained with respect to both XPS spectra are respectively designated $X^1$ and $X^2$.

It should be noted that, when the surface of a filter substrate is coated with a hydrophilic synthetic polymer, both the filter substrate and the hydrophilic synthetic polymer are present in the surface of the filter in ratios corresponding to the coating ratio of the filter substrate. The amount of the hydrophilic synthetic polymer present in the surface of the filter increases in accordance with an increase in the coating ratio. Therefore, the XPS spectrum of the surface of such a filter is an XPS spectrum of a mixture of the filter substrate and the hydrophilic synthetic polymer. For this reason, in the XPS spectrum of the surface of such a filter, the ratio (X) of the area of the peak ascribed to the preselected element or partial molecular structure to the area of a different peak which has been preselected as a standard is a value which is in the intermediate of the range of from $X^1$ to $X^2$. Based on this relationship between X, $X^1$ and $X^2$, the ratio between the amount of the filter substrate and the amount of the hydrophilic synthetic polymer both present in the surface of the filter (that is, the coating ratio) is determined.

Hereinbelow, a detailed explanation is made with respect to the above-mentioned method for determining the coating ratio, taking as an example a filter in which the filter substrate is comprised of polyethylene terephthalate (hereinafter referred to as "PET") and the hydrophilic synthetic polymer coating is comprised of poly(hydroxyethyl methacrylate) (hereinafter referred to as "PHEMA").

Both of PET and PHEMA are polymers composed of hydrogen, carbon and oxygen and, there is no element which is present in only one of the two polymers. Therefore, the amounts of PET and PHEMA present in the surface of the filter cannot be determined by a method which uses as an index the amount of an element which is present in only one of the two polymers. Therefore, in this case, the amounts of PET and PHEMA present in the surface of the filter are determined using the fact that PET and PHEMA are different from each other in the ratio of carbon atoms having different chemical linkages.

The carbon atoms which constitute PET and PHEMA can be classified into the following three groups a) to c):
  a) carbonyl carbon atom;
  b) carbon atom which is bonded directly to an oxygen atom only through a single bond; and
  c) carbon atom which is not directly bonded to an oxygen atom.

The structural unit which constitutes PET contains two carbonyl carbon atoms, two carbon atoms each of which is individually bonded directly to an oxygen atom only through a single bond, and six carbon atoms which are not directly bonded to an oxygen atom.

On the other hand, the structural unit which constitutes PHEMA contains one carbonyl carbon atom, two carbon atoms each of which is individually bonded directly to an oxygen atom only through a single bond, and three carbon atoms which are not directly bonded to an oxygen atom.

In each of PET and PHEMA, the ratio of the amount (number) of carbon atoms which are not directly bonded to an oxygen atom to the amount (number) of carbonyl carbon atoms is 3:1.

However, in PET, the ratio of the amount (number) of carbon atoms each of which is individually bonded directly to an oxygen atom only through a single bond to the amount (number) of carbonyl carbon atoms is 1:1, whereas in PHEMA, the ratio of the amount (number) of carbon atoms each of which is individually bonded directly to an oxygen atom only through a single bond to the amount (number) of carbonyl carbon atoms is 2:1.

The above-mentioned difference between PET and PHEMA in the ratio of the amounts (numbers) of carbon atoms of two different chemical linkages can be detected as a difference, between the XPS spectrum of PET and that of PHEMA, in the ratio between the intensities (areas) of two specific peaks.

That is, in an XPS spectrum of PET, a peak ascribed to carbon atoms each of which is individually bonded directly to an oxygen atom only through a single bond and a peak ascribed to carbonyl carbon atoms are observed, wherein the ratio of the intensity (area) of the former to the intensity (area) of the latter is 1:1. On the other hand, in an XPS spectrum of PHEMA, the above-mentioned two different peaks are observed, wherein the ratio of the intensity (area) of the former to the intensity (area) of the latter is 2:1.

When the surface of a non-woven fabric (as a filter substrate) comprised of PET fibers is coated with PHEMA, both PET and PHEMA are present in the surface of the filter in amounts corresponding to the coating ratio of the filter substrate. The amount of PHEMA present in the surface of the filter increases in accordance with an increase in the coating ratio. Therefore, the XPS spectrum of the surface of such non-woven fabric is an XPS spectrum of a mixture of PET and PHEMA. For this reason, in the XPS spectrum of the surface of such non-woven fabric, a peak ascribed to carbon atoms each of which is individually bonded directly to an oxygen atom only through a single bond and a peak ascribed to carbonyl carbon atoms are observed, wherein the ratio of the intensity (area) of the former to the intensity (area) of the latter is a value which is in the intermediate of the range of from the ratio in the case of an XPS spectrum of PET to the ratio in the case of an XPS spectrum of PHEMA. That is, with respect to the above-mentioned non-woven fabric, when the coating ratio is 0%, the above-mentioned intensity ratio (peak area ratio) is 1:1. The above-mentioned intensity ratio moves toward 2:1 in accordance with an increase in the coating ratio, and, when the coating ratio is 100%, the above-mentioned intensity ratio is 2:1.

Based on this fact, with respect to a filter of the present invention comprising a non-woven fabric of PET fibers (filter substrate) having coated thereon PHEMA, the coating ratio can be determined.

In general, in an XPS spectrum of each of PET, PHEMA and a filter of the present invention (wherein the filter comprises a non-woven fabric of PET fibers having coated thereon PHEMA), a plurality of peaks are observed approximately in the positions as shown in FIG. 1. In FIG. 1, peak a is ascribed to carbonyl carbon atoms, peak b is ascribed to carbon atoms each of which is individually bonded directly to an oxygen atom only through a single bond, and peak c is ascribed to carbon atoms which are not directly bonded to an oxygen atom.

The ratio of the area of peak a to the area of peak b of PET as a standard is defined as 1:x, the ratio of the area of peak a to the area of peak b of PHEMA as a standard is defined as 1:y, and the ratio of the area of peak a to the area of peak b of a sample filter is defined as 1:z. Then, the coating ratio of the sample filter is defined by the following formula:

Coating ratio $(\%) = \{|z-x|/|y-x|\} \times 100$.

With respect also to a filter in which the material of the filter substrate and the hydrophilic synthetic polymer are other than PET and PHEMA, respectively, the coating ratio can be obtained in substantially the same manner as described above.

In the present invention, the coating ratio which is obtained by the above-described method with respect to the surface of the filter is taken as the coating ratio of the filter of the present invention.

However, unless all surfaces of the elements constituting the filter substrate are not coated with the hydrophilic synthetic polymer, it is difficult to obtain a filter exhibiting a desired performance (i.e., not only the surface of the filter but also the surfaces of the elements present in the interior of the filter should be coated with the hydrophilic synthetic polymer). Therefore, in order to confirm that not only the surface of the filter but also the surfaces of the elements present in the interior of the filter are uniformly coated with the hydrophilic synthetic polymer, the below-described procedure is performed.

First, the filter is cut at an appropriately selected portion to obtain a cross section of the filter. In the cross section of the filter, 15 portions in total are randomly selected, wherein, among the 15 portions of the cross section, 5 portions are positioned in the vicinity of one surface of the filter; other 5 portions are positioned in the vicinity of the other surface of the filter; and the remaining 5 portions are positioned just in the middle of the distance between the both surfaces (namely, the above-mentioned one surface and the other surface) of the filter. With respect to each of the above-mentioned 15 portions, an XPS spectrum is obtained. The thus obtained 15 XPS spectra are examined to confirm that the shapes of the 15 XPS spectra are not greatly different from each other (i.e., substantially the same). By this method, the uniformity of the coating of the filter substrate in the thickness-wise direction of the filter is confirmed.

When the filter is cut, the filter substrate is exposed at a cross section of the filter. As a result, the apparent coating ratio with respect to the cross section is markedly lowered. This apparent lowering of the coating ratio greatly affects the XPS spectrum of the cross section of the filter. That is, in the XPS spectrum of the cross section, the intensities of the peaks ascribed to the hydrophilic synthetic polymer are lowered. Therefore, the shape of the XPS spectrum of the cross section of the filter is different from that in the case of the surface of the filter.

Further, the area of the cross section which is measured by XPS is inevitably small. For this reason, the XPS spectrum of the cross section tends to contain much noise and it is extremely difficult to obtain a clear XPS spectrum. Therefore, in the comparison of the XPS spectra of the above-mentioned 15 portions of the cross section of the filter, there is no meaning in making a comparison in the ratio between the intensities (areas) of the peaks. Therefore, in the comparison of the XPS spectra, when the XPS spectra are the same in the positions (i.e., chemical shifts) of the peaks, the XPS spectra are considered to have the same shape. When it is confirmed that the XPS spectra of 10 or more of the above-mentioned 15 portions of the cross section of the filter are considered to have the same shape, the filter substrate is considered to have a uniform coating of the polymer in the thickness-wise direction thereof.

In the present invention, it is preferred that the hydrophilic synthetic polymer has a molecular weight distribution wherein, in a gel permeation chromatogram of the polymer, the content of low molecular weight fractions having molecular weights which are ¼ or less of the peak-top molecular weight is 10% or less in terms of the percentage of an area in the peak which corresponds to the low molecular weight fractions, based on the entire area of the peak. The above-mentioned low molecular weight fractions correspond to components each having a low degree of polymerization, such as a dimer, a trimer, an oligomer or the like.

It has conventionally been known that the leukocyte removal efficiency tends to be lowered when the amount of the hydrophilic polymer coated on the filter substrate is increased. Therefore, it has been considered that a filter capable of satisfactorily functioning as a leukocyte removing filter cannot be obtained when the filter substrate is coated with a large amount of a hydrophilic polymer.

Further, the use of a large amount of the hydrophilic synthetic polymer for coating a filter is considered to pose a problem that the amount of the water-soluble component, which is dissolved-out from the coating material and gets mixed with the blood product obtained using the filter, becomes large and, hence, it is not desirable to administer the obtained blood product to a patient.

However, as a result of extensive and intensive studies of the present inventors, it has been found that the lowering of the leukocyte removal efficiency and the dissolution-out of the water-soluble component (which occur when the amount of the hydrophilic polymer coated on the filter substrate is increased for improving the coating ratio) are caused by the low molecular weight fractions contained in the hydrophilic synthetic polymer. In other words, it has been found that both of the above-mentioned problems are simultaneously solved by decreasing the amount of the low molecular weight fractions contained in the hydrophilic synthetic polymer.

In the present invention, there is no particular limitation with respect to the method for decreasing the amount of the low molecular weight fractions contained in the hydrophilic synthetic polymer so as to achieve the above-mentioned molecular weight distribution exhibited by the hydrophilic synthetic polymer. As an example of such a method, there can be mentioned a method in which the low molecular weight fractions contained in the hydrophilic synthetic polymer are removed by a conventional method, such as chromatography, phase separation or the like. In the present invention, the purification of the hydrophilic synthetic polymer (i.e., removal of the low molecular weight fractions) by "phase separation" is conducted by a method comprising subjecting a polymer solution to thermally induced phase separation and/or nonsolvent induced phase separation, to thereby separate the polymer solution into a polymer-rich phase and a polymer-lean phase, followed by collecting the thus separated polymer-rich phase. In this method, when the polymer solution is allowed to stand after the liquid—liquid phase separation for a certain period of time, the solution is completely separated into two phases, i.e., the polymer-rich phase and the polymer-lean phase. In the resultant solution, the lower phase is the polymer-rich phase due to the higher specific gravity thereof. Therefore, the polymer-rich phase can be collected by removing the polymer-lean (upper phase) or withdrawing the polymer-rich solution (lower phase).

In the present invention, the term "phase separation" means a phenomenon in which a polymer solution (having a temperature at which the polymer solution is in the form of a homogeneous solution) is separated into two polymer solution phases which are different in the polymer content and the molecular weight distribution of the polymer, i.e., the polymer-rich phase and polymer-lean phase. Whereas, the phase change (transition) to cause precipitation of a solid phase or a polymer does not fall within the definition of the "phase separation."

The term "thermally introduced phase separation" means an operation in which a polymer solution (having a temperature at which the polymer solution is in the form of a homogeneous solution) is cooled (or heated) at a predetermined rate, so that the solution is separated into a plurality of phases (for example, a plurality of different liquid phases; a liquid phase and a solid phase; and a plurality of different liquid phases and a solid phase). In the present invention, a plurality of different liquid phases are formed by the thermally introduced phase separation.

The term "nonsolvent induced phase separation method" means a method which comprises adding a non-solvent for a polymer to a polymer solution (having a temperature at which the polymer solution is in the form of a homogeneous solution) so as to separate the polymer solution into a plurality of phases (for example, a plurality of different liquid phases; a liquid phase and a solid phase; and a plurality of different liquid phases and a solid phase). In the present invention, a plurality of different liquid phases are formed by the nonsolvent induced phase separation.

In general, when it is intended to produce polymers having very high molecular weights, various measures are taken to increase the conversion of the monomers as much as possible and, hence, in some cases, polymers having very high molecular weights have a very low content of low molecular weight fractions. Therefore, it is possible that such polymers (hydrophilic synthetic polymers) having very high molecular weights exhibit the above-mentioned specific molecular weight distribution even without subjecting the polymers to any treatments.

The molecular weight distribution of the hydrophilic synthetic polymer is determined by subjecting the hydrophilic synthetic polymer to gel permeation chromatography (GPC). The conditions for the GPC analysis can be appropriately selected depending on the type of the hydrophilic synthetic polymer.

The determination of the molecular weight distribution of the hydrophilic synthetic polymer can be conducted before applying the hydrophilic synthetic polymer to the filter substrate. Alternatively, the determination of the molecular weight distribution of the hydrophilic synthetic polymer can be conducted with respect to the hydrophilic synthetic polymer extracted from the filter. The extraction of the hydrophilic synthetic polymer can be performed by immersing the filter in a solvent which does not dissolve the filter substrate but dissolves the hydrophilic synthetic polymer. When the hydrophilic synthetic polymer is a copolymer of 2-hydroxyethyl(meth)acrylate with dimethylaminoethyl (meth)acrylate, the extraction can be performed by using, as a solvent, N,N-dimethylformamide, an alcohol (such as methanol, ethanol or propanol) or a mixture thereof with water. After extracting the hydrophilic synthetic polymer from the filter, the extracted polymer is subjected to drying to thereby remove the solvent therefrom, and the determination of the molecular weight distribution of the polymer is conducted by the above-mentioned method.

Hereinbelow, an explanation is made on one example of a method for producing the filter (for selectively removing leukocytes) of the present invention.

The filter of the present invention for selectively removing leukocytes can be produced by, for example, a method comprising:

coating a filter substrate with the above-mentioned hydrophilic synthetic polymer either by applying a solution of the hydrophilic synthetic polymer in a solvent (hereinafter, referred to as a "polymer solution") to the surface of the filter substrate, or by immersing the filter substrate in the polymer solution, to thereby obtain a treated filter substrate; and removing the surplus amount of the polymer solution from the treated filter substrate by mechanical compression, gravity, centrifugation, blowing with a gas, or vacuum suction, or removing the solvent from the treated filter substrate by immersing the treated filter substrate in a nonsolvent therefor, and drying the resultant filter substrate, thereby obtaining a filter substrate having coated thereon the hydrophilic synthetic polymer.

The polymer solution is prepared, for example, by placing a solvent and a hydrophilic synthetic polymer in a container equipped with a temperature controller, followed by dissolving the polymer in the solvent by using a mixing device, such as an agitator.

When the hydrophilic synthetic polymer is a copolymer of 2-hydroxyethyl(meth)acrylate and dimethylaminoethyl (meth)acrylate, examples of solvents which can be used for dissolving the hydrophilic synthetic polymer include glycols, such as ethylene glycol and diethylene glycol; alcohols, such as methanol, ethanol, n-propyl alcohol, isopropyl alcohol, n-butyl alcohol, isobutyl alcohol and t-butyl alcohol; N,N-dimethylformamide and methyl cellosolve. These solvents may be used individually or in combination. Further, each of these solvents can be used in the form of a mixture thereof with water.

The hydrophilic synthetic polymer concentration of the polymer solution may vary depending on the type of the filter substrate and the type of the hydrophilic synthetic polymer. For example, when the filter substrate comprises a non-woven fabric of polyethylene terephthalate and the hydrophilic synthetic polymer is a copolymer of 2-hydroxyethyl(meth)acrylate with dimethylaminoethyl (meth)acrylate, it is preferred that the polymer concentration is from 2 to 30% by weight, more advantageously from 5 to 20% by weight. When the polymer concentration is less than 2% by weight, there is a tendency that the coating ratio would not reach 70%, leading to a lowering of the platelet passage ratio. On the other hand, when the polymer concentration is more than 30% by weight, there is a tendency that the viscosity of the polymer solution becomes too high, so that the coating operation becomes difficult.

When the hydrophilic synthetic polymer is applied to the filter substrate, the actual amount of the hydrophilic synthetic polymer which is coated on the filter substrate (hereinafter, referred to as an "amount of the coating") is adjusted to a predetermined value. The amount of the coating can be adjusted by either a post-measurement method in which a filter substrate is coated with an excessive amount of a hydrophilic synthetic polymer, followed by removal of a surplus amount of the coating, to thereby adjust the amount of the coating to a desired level; or a pre-measurement method in which a polymer solution having a polymer concentration adjusted to form a desired amount of the coating on a filter substrate is applied to the filter substrate.

Further, in the present invention, either after applying the polymer solution to the filter substrate or after immersing the filter substrate in the polymer solution, the resultant filter substrate may be subjected to nipping to thereby uniformly coat the filter substrate in the thickness-wise direction thereof. The term "nipping" used in the present invention means an operation of squeezing out the surplus amount of the polymer solution and the residual solvent remaining in the filter substrate after applying the polymer solution to the filter substrate or after immersing the filter substrate in the polymer solution. Specifically, the nipping operation is conducted by passing the coated or immersed filter substrate through a gap (i.e., nip) between two nipping rolls, which gap has a predetermined width.

The width of the nip (gap between the two nipping rolls) is appropriately selected within the values, each of which is not more than the thickness of the filter substrate and would not cause damage to the filter substrate. For example, when the porosity of the filter substrate is in the range of from 50 to 95%, it is preferred that the nip (gap between the two nipping rolls) has a width of 10 to 100% of the thickness of the filter substrate. When the nip is less than 10% of the thickness of the filter substrate, the filter substrate is likely to be damaged. On the other hand, when the nip is larger than the thickness of the filter substrate, a difference in the leukocyte removal efficiency between the portions of the filter is likely to become large.

As an example of the method for drying the coated filter substrate, there can be mentioned a method in which a filter substrate is dried in an atmosphere of a dry gas or under a reduced pressure, and at ambient temperature or while heating.

When the affinity between the filter substrate and the hydrophilic synthetic polymer is high, the hydrophilic synthetic polymer concentration of the polymer solution and the amount of the coating are in a proportional relationship and, thus, the higher polymer concentration of the polymer solution, the larger the amount of the coating formed on the filter substrate. Further, when the affinity between the filter substrate and the hydrophilic synthetic polymer is high, the coating ratio is increased in accordance with the increase in the amount of the coating. Therefore, when the affinity between the filter substrate and the hydrophilic synthetic polymer is high, the coating ratio can be adjusted by varying the hydrophilic synthetic polymer concentration of the polymer solution.

Alternatively, it is also possible to increase the coating ratio by introduction of a functional group having a lone electron pair into the surface of the filter substrate. Such a functional group can be introduced by the above-mentioned energy beam irradiation (such as an electron beam irradiation and a γ-ray irradiation) or the above-mentioned electrical discharge treatment (such as a corona discharge treatment and a plasma treatment) or oxidation treatment using a chemical agent and the like.

When the thus obtained filter of the present invention is contacted with human whole blood, leukocytes contained in the whole blood are selectively adsorbed on the filter. On the other hand, plasma, red cells and platelets contained in the whole blood pass through the filter. As a result, a leukocyte-removed blood suspension is obtained.

For preparing a leukocyte-removed blood suspension by using the filter of the present invention, in general, the filter is packed in a conventional container for a blood filtration filter which has an inlet and outlet for blood.

For filtration of blood, a single filter of the present invention may be used or, alternatively, a stack of a plurality of filters (including the filter(s) of the present invention) may be used, depending on the thickness of the filter(s). With respect to the stacked filters, the stacked filters may include conventional filters, and the number of the filters may vary depending on the conditions used for filtration of blood, and, hence, is not particularly limited. However, generally, several to several tens of filters are used. Further, when the filter substrates of the stacked filters comprise woven or non-woven fabrics, the type of the fabric and/or the average pore diameter may differ between the filters.

Further, when the stacked filters are used, for obtaining a satisfactory platelet passage ratio, it is preferred that, among the filters used in the stack, at least a filter having the smallest average pore diameter or a filter comprising a fabric having the smallest average fiber diameter is the filter of the present invention, namely the filter comprising a filter substrate having coated thereon a hydrophilic synthetic polymer in a coating ratio of 70% or more with respect to the overall surface of the filter substrate. It is more preferred that all of the filters used in the stack are filters of the present invention.

BEST MODE FOR CARRYING OUT THE INVENTION

Hereinbelow, the present invention will be described in more detail with reference to Examples, Comparative Examples, Reference Comparative Example and Reference Examples, but they should not be construed as limiting the scope of the present invention.

In the Examples, Comparative Examples and Reference Examples, various properties were evaluated in accordance with the following methods.

1) Method for Determining the Weight Average Molecular Weight and Molecular Weight Distribution of a Hydrophilic Polymer The weight average molecular weight and molecular weight distribution of a hydrophilic polymer are determined by GPC, as follows. LiBr (lithium bromide) is dissolved in N,N-dimethylformamide to obtain a 1 mM LiBr solution (hereinafter referred to as "solution A"), and a hydrophilic polymer is dissolved in solution A to thereby obtain a polymer solution (polymer concentration: 1 mg of polymer per ml of the solvent (solution A)). The polymer solution is analyzed at 40° C. by GPC using a GPC apparatus (Apparatus: HLC-8020+program for analysis: GPC-LALLS Ver. 2.03; both manufactured and sold by Tosoh Corp., Japan) and an RI detector (differential refractometer). The GPC apparatus is equipped with a guard column (TSKguardcolumn $H_{XL}$-H, manufactured and sold by Tosoh Corp., Japan) and two main columns (first stage column: TSKgel $GMH_{XL}$ B0032, manufactured and sold by Tosoh Corp., Japan; and second stage column: TSKgel α-M B0011, manufactured and sold by Tosoh Corp., Japan). The GPC analysis is conducted under conditions wherein solution A is used as a mobile phase, and the column temperature is 40° C. The weight average molecular weight and molecular weight distribution of the polymer are calculated using the relationship of the molecular weights (known values) of a set of poly(methyl methacrylate) samples to the GPC retention times (measured values) of the set of poly(methyl methacrylate) samples (wherein the set of poly(methyl methacrylate) samples is M-M-10 Set, manufactured by Polymer Laboratories, England, and sold by GL Science Inc., Japan).

2) Method for Determining the Coating Ratio of the Surface of the Filter Substrate Having Coated Thereon a Hydrophilic Polymer The coating ratio of the surface of the filter substrate having coated thereon a hydrophilic polymer is determined using a sample filter which is obtained by cutting a filter into a square having a size of about 1 cm×about 1 cm.

The sample filter is subjected to X-ray photoelectron spectroscopy (XPS). X-ray photoelectron spectroscopy (XPS) is also conducted with respect to each of a PET (polyethylene terephthalate) standard (a film or a plate) and a hydrophilic polymer standard (in the form of a pellet obtained by pelletizing a powder of the hydrophilic polymer), wherein the hydrophilic polymer is a 2-hydroxyethyl methacrylate-dimethylaminoethyl methacrylate copolymer or a 2-hydroxyethyl methacrylate-diethylaminoethyl methacrylate copolymer. The XPS is conducted using an XPS spectrometer (AXIS-Ultra, manufactured and sold by Shimadzu Corporation, Japan), and $K_\alpha$ monochromatic ray (300 W) of Al is used as an X-ray source. The XPS analysis was performed under conditions wherein the analysis mode is narrow scanning with neutralization of electrostatic charge, wherein the pass energy is 10 eV and the area analyzed is 700 μm×300 μm.

FIG. 1 is one example of a narrow scan X-ray photoelectron spectrum obtained by analyzing the filter of the present invention in the above-mentioned manner, wherein the intensity (a.u. (angstrom unit)) is shown against the binding energy (eV).

(Details of Peak Resolution)

A computer software called "The Eclipse Datasystem Version 2.1" (manufactured and sold by Fisons Surface Systems plc, England) is used for peak resolution with respect to X-ray photoelectron spectra. The operation for peak resolution using this computer software comprises the following steps 1 to 4.

Step 1. In an X-ray photoelectron spectrum (XPS spectrum), the range to be subjected to peak resolution is determined so that all of peaks a to c as shown in the X-ray photoelectron spectrum of FIG. 1 are contained in the range. Then, the background noises in the determined range of the XPS spectrum are removed by the Shirley method.

Step 2. Conditions for peak resolution are set so that three mixed Gaussian/Lorentzian peaks (which respectively correspond to peaks a, b and c in FIG. 1) will appear in the range for peak resolution determined in Step 1 above (wherein peak a is ascribed to the underlined carbon atom in each of O—C̲=O linkages; peak b is ascribed to the underlined carbon atom in each of C—C̲—O linkages; and peak c is ascribed to the underlined carbon atom in each of C—C̲—C linkages and C—C̲H₃ linkages). The peak centers, peak heights, half widths and Gaussian/Lorentzian mixing ratios of the three mixed Gaussian/Lorentzian peaks are used as parameters for peak resolution.

Step 3. The peak resolution is performed using the minimum Chi-Square method, and the ratio of the area of peak a to the area of peak b is determined. The peak resolution is performed under the following limitations (1) and (2).

Limitation (1): With respect to the difference (Difference I) between the half width of peak a and the half width of peak b both appearing in the XPS spectrum of the sample filter and the difference (Difference II) between the half width of peak a and the half width of peak b both appearing in the XPS spectrum of the PET standard, the "Difference I" is within the range of the "Difference II"±0.1 eV.

Limitation (2): The Gaussian/Lorentzian mixing ratios of peaks a and b are within the range of from 0.2 to 0.5, with the proviso that the Gaussian/Lorentzian mixing ratio of peak b is within the range of the Gaussian/Lorentzian mixing ratio of peak a±0.15. The Gaussian/Lorentzian mixing ratio of peak c is in the range of from 0.2 to 0.55.

Step 4. The ratio of the area of peak a to the area of peak b of the PET standard is defined as 1:x, the ratio of the area of peak a to the area of peak b of the hydrophilic polymer standard (prepared by pelletizing a powder of the hydrophilic polymer) is defined as 1:y, and the ratio of the area of peak a to the area of peak b of the sample filter is defined as 1:z. Then, the coating ratio of the sample filter is calculated by the following formula:

Coating ratio (%)={|z−x|/|y−x|}×100

The sample filter used has a residual solvent content of not more than 1 ppm and a thickness of 0.1 mm or more.

3) The Method for Measuring the Uniformity of the Coating Ratio of the Filter Substrate (Having Coated Thereon a Hydrophilic Polymer) in the Thickness-Wise Direction The XPS analysis for determining the coating ratio is conducted in substantially the same manner as in item 2) above ("Method for determining the coating ratio of the surface of the filter substrate having thereon a hydrophilic polymers"), except that the narrow scanning is conducted under conditions wherein the pass energy is 40 eV and the area analyzed is 27 μm φ.

The measuring positions are preselected as follows. A filter is cut to obtain a cross section of the filter. In the cross section of the filter, 15 portions in total are randomly preselected, wherein, among the 15 portions of the cross section, 5 portions are positioned in the vicinity of one surface of the filter; other 5 portions are positioned in the vicinity of the other surface of the filter; and the remaining 5 portions are positioned just in the middle of the distance between the above-mentioned one and the other surfaces of the filter. Each of the above-mentioned 15 portions is analyzed.

4) Method for Determining the Specific Surface Area

The specific surface area of the filter is determined using "Accusorb 2100E" (manufactured and sold by Shimadzu Corporation, Japan) or an apparatus substantially the same as this. Specifically, 0.50 to 0.55 g of a filter substrate is weighed and packed in a test tube. The filter substrate in the test tube is degassed in the Accusorb under a reduced pressure of $1 \times 10^{-4}$ mmHg (in vacuo) for 20 hours, and then the specific surface area is measured under conditions wherein krypton gas is used as an adsorption gas and the gas adsorption is performed while cooling with liquid nitrogen.

5) Method for Conducting an Acute Toxicity Test (Preparation of a Sample Solution)

A 500 ml glass container which has been qualified in the alkali dissolution test of the "tests for glass containers for injection" described in the Japanese Pharmacopoeia is provided. To the glass container are added 0.2 g of a polymer (amount of residual solvent: not more than 1 ppm) in the form of a film having a thickness of 0.22 mm to 0.26 mm (the film has been cut into pieces each having a size of approximately 2 cm$^2$) and 300 ml of a physiological saline solution (physiological saline solution prescribed in the Japanese Pharmacopoeia; manufactured and sold by Otsuka Pharmaceutical Co., Ltd., Japan). The glass container is then hermetically sealed and placed in a shaker/incubator (WATER BATH INCUBATOR BT-47, manufactured and sold by YAMATO SCIENTIFIC Co., Ltd., Japan) and incubated with shaking (shaking rate: 120 times/minute) at 70° C.±5° C. for 1 hour. Then, the glass container with its content is allowed to stand still until it is cooled to room temperature. Then, the polymer is taken out from the physiological saline solution, and the remaining physiological saline solution is used as a sample solution.

(Acute Toxicity Test)

The acute toxicity test is conducted in accordance with item V-7 of the Standard for Approval of Dialysistype Artificial Kidney, Japan. 50 ml/kg of the test solution is intravenously administered to ten male mice (weight: 17 g to 23 g) of a homogeneous line or pure line. After the injection, the mice are observed for 5 days to check whether or not any disorder or death of mice occurs.

EXAMPLE 1

(Preparation of a Polymer Solution)

A uniform solution comprising 91.85% by weight of ethanol and, dissolved therein, 8.15% by weight of a copolymer was prepared by dissolving the copolymer in ethanol at 40° C., wherein the copolymer was comprised of 97 mol % of 2-hydroxyethyl methacrylate and 3 mol % of dimethylaminoethyl methacrylate (weight average molecular weight: 650,000; content of basic nitrogen atoms: 0.32% by weight; molar amount of nonionic hydrophilic groups: 97 mol %; molar amount of basic nitrogen atoms: 3 mol %; peak-top molecular weight: 2.88×10 and content of low molecular weight polymers: 4.9%).

The above-mentioned 2-hydroxyethyl methacrylate-dimethylaminoethyl methacrylate copolymer having a weight average molecular weight of 650,000, a peak-top molecular weight of $2.88 \times 10^5$ and a content of low molecular weight polymers of 4.9% was obtained by the following method.

There was provided a copolymer solution (38% by weight of a copolymer in ethanol) wherein the copolymer was comprised of 97 mol % of 2-hydroxyethyl methacrylate and 3 mol % of dimethylaminoethyl methacrylate (the copolymer was a crude copolymer immediately after the production thereof by a copolymerization reaction) (weight average molecular weight: 548,000; content of basic nitrogen atoms: 0.32% by weight; molar amount of nonionic hydrophilic groups: 97 mol %; molar amount of basic nitrogen atoms: 3 mol %; peak-top molecular weight: $2.78 \times 10^5$; and content of low molecular weight polymers: 12.6%). To the copolymer solution was added ethanol in a volume which was 4 times the volume of the copolymer solution, and the resultant mixture was heated at 40° C. to thereby obtain a uniform solution. The obtained solution was allowed to stand at room temperature of 25° C. for 12 hours to thereby effect a liquid—liquid phase separation by the thermally induced phase separation method. The thus separated polymer-rich phase was recovered as a polymer-rich solution. The recovered polymer-rich solution was subjected to spray-drying to thereby remove the solvent contained in the solution.

(Coating)

Figure 3:
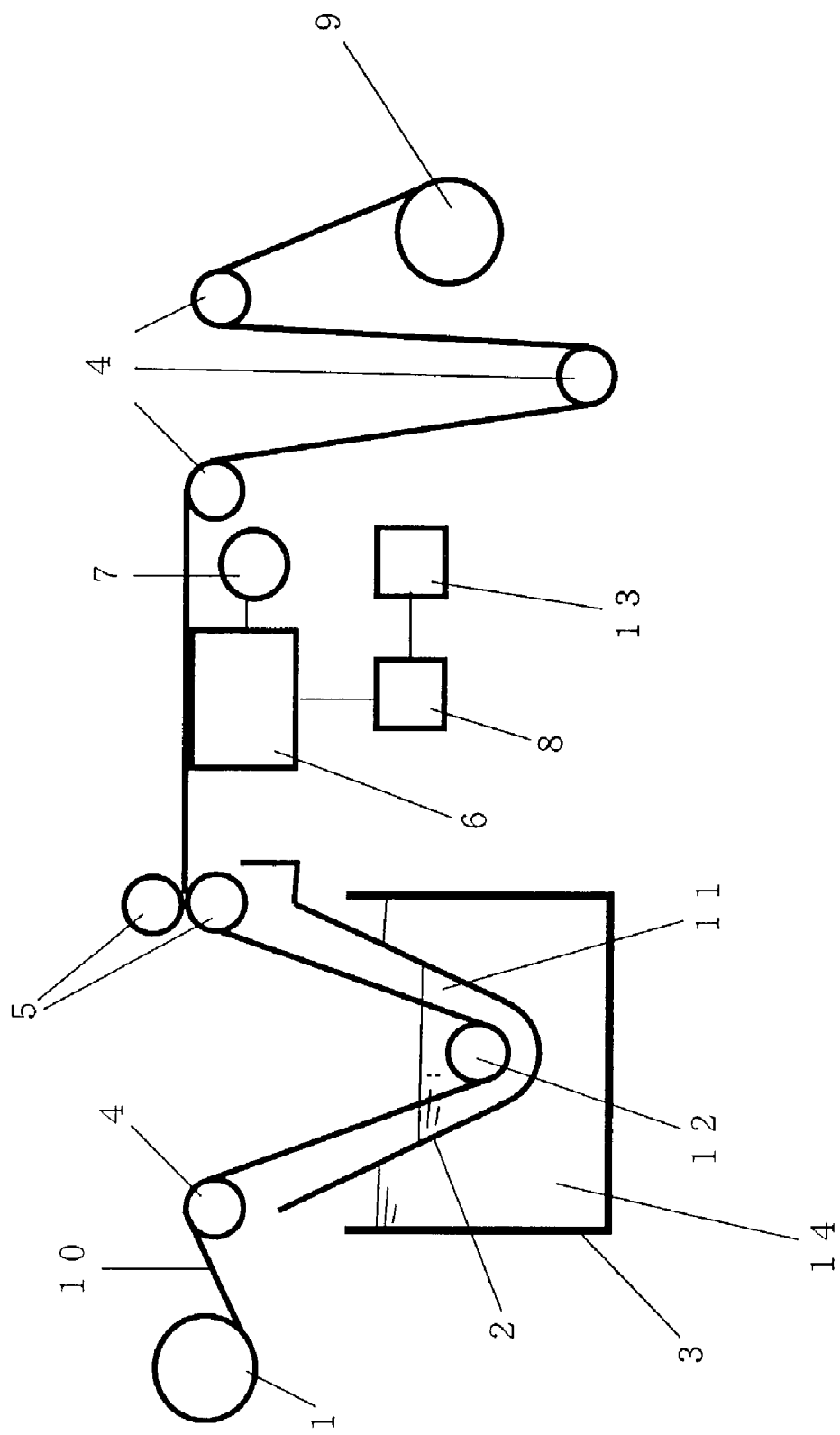
FIG. 3 is an explanatory view of an example of equipment used for producing the filter of the present invention for selectively removing leukocytes.

FIG. 3 is an explanatory view of the equipment used for producing the filter of the present invention for selectively removing leukocytes. This equipment comprises:

means 2 (i.e., vessel of a polymer solution for coating) for coating filter substrate 10 with polymer solution 11;

means 5 for nipping (i.e., rolls for nipping);

means 6 for suction (i.e., suction apparatus for removing an excess polymer solution remaining in the filter substrate), which will be in contact with the surface of the coated filter substrate immediately after nipping;

trapping apparatus 8 for an excess polymer solution removed from the filter substrate; and pressure controller 13 which is connected to suction means 6 though trapping apparatus 8.

There is no particular limitation with respect to means 2 for coating filter substrate 10 with polymer solution 11, so long as the contacting between polymer solution 11 and filter substrate 10 can be effected. When it is intended to perform the coating by impregnating filter substrate 10 with polymer solution 11, for fully contacting filter substrate 10 with polymer solution 11, an additional device (such as roll 12 for impregnation) can be used.

Using the equipment of FIG. 3, 15 m of a non-woven fabric (as filter substrate 10), which was comprised of polyethylene terephthalate fibers having an average fiber diameter of 1.2 μm and which had a weight of 40 g/m², a porosity of 79%, a thickness of 0.24 mm, a width of 150 mm and a specific surface area of 2.01 m²/g, was subjected to coating treatment by the following method.

Filter substrate 10 was continuously immersed in the above-mentioned polymer solution 11 at 40° C. and, then, taken out from polymer solution 11, followed by nipping which was conducted by passing the filter substrate through the gap between rolls 5,5 for nipping, which are arranged so that the distance between rolls 5,5 was 0.13 mm. The resultant nipped filter substrate was subjected to suction for removing a surplus amount of polymer solution 11 remaining in the nipped filter substrate. Specifically, using suction apparatus 6 having a slit (hole) (not shown) for suction (wherein the slit had a length of 140 mm and a width of 3 mm), one surface of the filter precursor was sucked to remove a surplus amount of polymer solution 11 from the filter substrate under an absolute pressure of 710 mmHg, while passing the filter substrate through the slit in a direction perpendicular to the slit and while winding up the filter substrate after the suction operation. In the treatment using the apparatus of FIG. 3, the operation rate (i.e., amount (m) of the filter substrate subjected to the above-mentioned nipping and suction per minute) was adjusted to and maintained at 3 m/min. The wound-up filter substrate after the suction operation was subjected to vacuum drying at 25° C. for 16 hours to thereby obtain a filter. With respect to the obtained filter, the amount of ethanol remaining in the filter was 1 ppm or less. The amount of the polymer coated on the filter substrate 10 (hereinafter referred to as the "amount of the coated polymer") is shown in Table 1 in terms of the amount of the polymer coated per unit specific surface area (mg/m²) of the filter substrate.

(Test for Evaluating the Blood Filtering Performance of the Filter)

With respect to the obtained filter (having a width of 150 mm), edge portions (each having a width of 10 mm) at longer sides thereof were cut off so that the width of the filter became 130 mm. From arbitrarily selected portions of the filter were cut out circular pieces, each having a diameter of 25 mm. Of the obtained circular pieces of the filter, 4 pieces were packed into a cylindrical filter holder (manufactured and sold by Shibata Scientific Technology Ltd., Japan) so that the packing density was 0.16 g/cm³, to thereby obtain a filter system.

Through the obtained filter system was flowed 6 ml of human blood (which contained CPD (citrate-phosphate dextrose) and had been stored for one day after collection) (hereinafter, the human blood before being flowed through the filter system is referred to as "non-filtered blood") at room temperature by means of a syringe pump, wherein the flow rate was constantly maintained at 2.7 ml/min, to thereby obtain a filtered blood.

With respect to each of the above-mentioned non-filtered blood and filtered blood, the leukocyte concentration and platelet concentration were measured as follows.

1 ml of the blood was mixed with 9 ml of Leukoplate solution as a hemolytic agent, and the resultant mixture was subjected to centrifugation, to thereby separate the mixture into into a precipitate and a supernatant. Then, a portion of the supernatant was removed by decantation to obtain a liquid having a volume of 1 ml. With respect to the obtained liquid, the leukocyte concentration was measured by means of a blood cell counting chamber (the measured leukocyte concentration was defined as the leukocyte concentration of the blood).

On the other hand, the platelet concentration of the blood was measured by means of an automatic multi-parameter corpuscle counter (K-4500; manufactured and sold by SYSMEX CORPORATION, Japan), wherein Stomatolyser (manufactured and sold by SYSMEX CORPORATION, Japan) was used as a hemolytic agent.

The leukocyte removal ratio and the platelet passage ratio were calculated in accordance the following formulae.

$$\text{Leukocyte removal ratio (\%)} = \left(1 - \frac{\text{Leukocyte concentration of the filtered blood}}{\text{Leukocyte concentration of the non-filtered blood}}\right) \times 100$$

$$\text{Platelet passage ratio (\%)} = \frac{\text{Platelet concentration of the filtered blood}}{\text{Platelet concentration of the non-filtered blood}} \times 100$$

The above-mentioned test for evaluating the blood filtration performance of the filter was conducted five times, and each of the leukocyte removal ratio and the platelet passage ratio was obtained as an average of the values obtained in the five runs of the test. The leukocyte removal ratio and the platelet passage ratio are shown in Table 1, together with the coating ratio and the amount of the coated polymer.

The obtained filter exhibited a high leukocyte removal efficiency and a high platelet passage ratio. Specifically, in each run of the test for evaluating the blood filtering performance, the platelet passage ratio was more than 80% (the highest value: 92.0%; the lowest value: 88.2%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

EXAMPLE 2

Substantially the same procedure as in Example 1 was repeated, except that in place of the copolymer solution used in Example 1, the coating of the filter substrate was conducted using a uniform solution comprising 96.34% by weight of ethanol and, dissolved therein, 3.66% by weight of the copolymer used in Example 1, which solution was prepared by dissolving the copolymer in ethanol at 40° C. The results are shown in Table 1. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 84.5%; the lowest value: 80.3%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

COMPARATIVE EXAMPLE 1

Substantially the same procedure as in Example 1 was repeated, except that in place of the copolymer solution used in Example 1, the coating of the filter substrate was conducted using a uniform solution comprising 98.75% by weight of ethanol and, dissolved therein, 1.25% by weight of the copolymer used in Example 1, which solution was prepared by dissolving the copolymer in ethanol at 40° C. The results are shown in Table 1. The test for evaluating the blood filtering performance was conducted five times, and, in each run of the test, the platelet passage ratio was less than 80% (the highest value: 79.2%; the lowest value: 59.8%). An XPS analysis of a cross section of the filter showed that the filter substrate had a uniform coating of a polymer in the thickness-wise direction thereof.

COMPARATIVE EXAMPLE 2

Substantially the same procedure as in Example 1 was repeated, except that in place of the copolymer solution used in Example 1, the coating of the filter substrate was conducted using a uniform solution comprising 99.75% by weight of ethanol and, dissolved therein, 0.25% by weight of the copolymer used in Example 1. The results are shown in Table 1. The test for evaluating the blood filtering performance was conducted five times, and, in each run of the test, the platelet passage ratio was less than 80% (the highest value: 38.2%; the lowest value: 13.9%). An XPS analysis of a cross section of the filter showed that the filter substrate had a uniform coating of a polymer in the thickness-wise direction thereof.

COMPARATIVE EXAMPLE 3

Substantially the same procedure as in Example 1 was repeated, except that in place of the copolymer solution used in Example 1, the coating of the filter substrate was conducted using a uniform solution comprising 99.87% by weight of ethanol and, dissolved therein, 0.13% by weight of the copolymer used in Example 1. The results are shown in Table 1. The test for evaluating the blood filtering performance was conducted five times, and, in each run of the test, the platelet passage ratio was less than 80% (the highest value: 24.8%; the lowest value: 5.8%). An XPS analysis of a cross section of the filter showed that the filter substrate had a uniform coating of a polymer in the thickness-wise direction thereof.

EXAMPLE 3

Substantially the same procedure as in Example 1 was repeated, except that in place of the polymer used in Example 1, the coating of the filter substrate was conducted using a copolymer comprising 95 mol % of 2-hydroxyethyl methacrylate and 5 mol % of diethylaminoethyl methacrylate (weight average molecular weight: 780,000; content of basic nitrogen atoms: 0.53% by weight; molar amount of nonionic hydrophilic groups: 95 mol %; molar amount of basic nitrogen atoms: 5 mol %; peak-top molecular weight: $3.20 \times 10$; and content of low molecular weight polymers: 6.2%). The results are shown in Table 2. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 89.6%; the lowest value: 86.8%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

The above-mentioned 2-hydroxyethyl methacrylate-diethylaminoethyl methacrylate copolymer (having a weight average molecular weight of 780,000, a peak-top molecular weight of $3.20 \times 10^5$ and a content of low molecular weight polymers of 6.9%) was obtained by the following method.

There was provided a copolymer solution (40% by weight of a copolymer in ethanol), wherein the copolymer was comprised of 95 mol % of 2-hydroxyethyl methacrylate and 5 mol % of diethylaminoethyl methacrylate (the copolymer was a crude copolymer immediately after the production thereof by a copolymerization reaction) (weight average molecular weight: 725,000; content of basic nitrogen atoms: 0.53% by weight; molar amount of nonionic hydrophilic groups: 95 mol %; molar amount of basic nitrogen atoms: 5 mol %; peak-top molecular weight: $3.03 \times 10^5$; and content of low molecular weight polymers: 15.5%). To the copolymer solution was added ethanol in a volume which was 4 times the volume of the copolymer solution, and the resultant mixture was heated at 40° C. to thereby obtain a uniform solution. The obtained solution was allowed to stand at room temperature (25° C.) for 12 hours to thereby effect a liquid—liquid phase separation by the thermally induced phase separation method, to thereby separate the solution into a polymer-rich phase and a polymer-poor phase. The thus separated polymer-rich phase was recovered as a polymer-rich solution. The recovered polymer-rich solution was subjected to spray-drying to thereby remove the solvent contained in the solution.

EXAMPLE 4

Substantially the same procedure as in Example 1 was repeated, except that in place of the non-woven fabric used in Example 1, a non-woven fabric (weight: 40 g/m$^2$, porosity: 75%, thickness: 0.23 mm, width: 150 mm, specific surface area: 1.98 m$^2$/g) comprised of poly(trimethylene terephthalate) fibers having an average fiber diameter of 1.2 μm was used as the filter substrate. The results are shown in Table 2. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 86.4%; the lowest value: 82.5%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

EXAMPLE 5

(Preparation of a Polymer Solution)

Substantially the same procedure as in Comparative Example 1 was repeated, except that in place of ethanol used in Comparative Example 1, a denatured alcohol (trade name: AP-7, manufactured and sold by Japan Chemical Product Company Limited, Japan) comprising 85.5% by weight of ethanol, 9.6% by weight of n-propyl alcohol and 4.9% by weight of isopropyl alcohol (water content: 0.2% by weight or less) was used.

(Pretreatment of a Filter Substrate)

The same filter substrate as used in Example 1 was subjected to corona discharge treatment. Specifically, each surface of the filter substrate was subjected to corona discharge treatment twice, which was performed by means of a discharge device AGI-020S (manufactured and sold by Kasuga Electric Works Ltd., Japan) under conditions wherein the discharge amount was 330 W/(m$^2$/min), the discharge intensity was 80 W/cm$^2$, the voltage was 20 kV and the distance between the electrode and the filter substrate was 3 mm.

The filter substrate after the corona discharge treatment was subjected to coating and test for evaluating the blood filtering performance thereof, which were conducted in substantially the same manner as in Example 1. The results are shown in Table 2. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 84.7%; the lowest value: 80.0%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

EXAMPLE 6

Substantially the same procedure as in Example 5 was repeated, except that the filter substrate was subjected to electron beam irradiation (instead of corona discharge treatment) under conditions wherein the acceleration voltage was 5 MV and the absorbed dose was 100 kGy. The results are shown in Table 2. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 85.3%; the lowest value: 80.5%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

EXAMPLE 7

Substantially the same procedure as in Example 5 was repeated, except that the filter substrate after the corona discharge treatment was further subjected to electron beam irradiation in substantially the same manner as in Example 6. The results are shown in Table 2. The obtained filter exhibited a high leukocyte removal efficiency and a high platelet passage ratio. Specifically, the test for evaluating the blood filtering performance was conducted five times, and, in each run of the test, the platelet passage ratio was more than 80% (the highest value: 86.6%; the lowest value: 81.1%). Further, the hematocrit of the filtered blood was the same as that of the non-filtered blood. The amount of materials dissolved from the filter was substantially the same as that of materials dissolved from the filter substrate itself. An XPS analysis of a cross section of the filter showed that the filter substrate had a uniform coating of a polymer in the thickness-wise direction thereof.

COMPARATIVE EXAMPLE 4

Substantially the same procedure as in Example 5 was repeated, except that the corona discharge treatment was not performed. The results are shown in Table 3. The test for evaluating the blood filtering performance was conducted five times, and, in each run of the test, the platelet passage ratio was less than 80% (the highest value: 79.5%; the lowest value: 63.6%). An XPS analysis of a cross section of the filter showed that the filter substrate had a uniform coating of a polymer in the thickness-wise direction thereof.

REFERENCE COMPARATIVE EXAMPLE

In accordance with the working Examples of Japanese Patent No. 2854857, it was tried to dissolve chitosan in a 1% aqueous acetic acid solution in an attempt to prepare an aqueous chitosan solution. Specifically, chitosan (degree of deacetylation: 85.2%, average molecular weight: 200,000) (code number: C0831, manufactured and sold by Tokyo Kasei Kogyo Co. Ltd., Japan) was added to three 1% aqueous acetic acid solutions to obtain 3 aqueous mixtures respectively having chitosan contents of 1% by weight, 3% by weight and 5% by weight, and each of the obtained aqueous mixtures was individually agitated at 10° C., 25° C., 40° C., 60° C., 80° C. or 100° C. by means of a stirrer or a Henschel mixer.

However, in the case of each of the aqueous mixtures respectively having chitosan contents of 3% by weight and 5% by weight, the chitosan absorbed the aqueous acetic acid solution, but could not be dissolved in the aqueous acetic acid solution. Even in the case of the aqueous mixture having a chitosan content of 1% by weight, a part of the chitosan remained undissolved in the form of a jelly- or pudding-like solid, and therefore a solution could not be obtained.

COMPARATIVE EXAMPLE 5

Substantially the same procedure as in Example 3 was repeated, except that in place of the copolymer solution used in Example 3, a uniform solution comprising 98.75% by weight of ethanol and, dissolved therein, 1.25% by weight of the copolymer used in Example 3 was used. The results are shown in Table 3. The test for evaluating the blood filtering performance was conducted five times, and, in each run of the test, the platelet passage ratio was less than 80% (highest value: 77.9%; lowest value: 61.2%). An XPS analysis of a cross section of the filter showed that the filter substrate had a uniform coating of a polymer in the thickness-wise direction thereof.

COMPARATIVE EXAMPLE 6

Substantially the same procedure as in Comparative Example 5 was repeated, except that in place of the non-woven fabric used in Comparative Example 5, a non-woven fabric comprised of polyethylene terephthalate fibers having an average fiber diameter of 1.8 μm (weight: 40 g/m², void ratio: 76%, thickness: 0.23 mm, width: 150 mm, specific surface area: 1.50 m²/g) was used. The results are shown in table 3. A comparison of the obtained results with those obtained in Comparative Example 5 showed that when the diameter of the fibers of the filter substrate is increased, although the platelet passage ratio of the filter becomes high, the leukocyte removal efficiency of the filter is greatly lowered. An XPS analysis of a cross section of the filter showed that the filter substrate had a uniform coating of a polymer in the thickness-wise direction thereof.

COMPARATIVE EXAMPLE 7

Substantially the same procedure as in Comparative Example 1 was repeated, except that the crude hydrophilic copolymer (before purification) mentioned in Example 1 was used. The results are shown in Table 3. The leukocyte removal ratio and platelet passage ratio of the obtained filter were low, as compared to those in Comparative Example 1. An XPS analysis of a cross section of the filter showed that the filter substrate had a uniform coating of a polymer in the thickness-wise direction thereof. A comparison of the obtained results with those in Comparative Example 1 showed that when the content of low molecular weight polymers in the hydrophilic copolymer is increased, the leukocyte removal ratio is lowered.

COMPARATIVE EXAMPLE 8

Substantially the same procedure as in Comparative Example 2 was repeated, except that the crude hydrophilic copolymer (before purification) mentioned in Example 1 was used. The results are shown in Table 3. The leukocyte removal ratio and platelet passage ratio of the obtained filter were low, as compared to those in Comparative Example 2. An XPS analysis of a cross section of the filter showed that the filter substrate had a uniform coating of a polymer in the thickness-wise direction thereof. A comparison of the obtained results with those in Comparative Example 2 showed that when the content of low molecular weight polymers in the hydrophilic copolymer is increased, the leukocyte removal ratio is lowered.

EXAMPLE 8

Substantially the same procedure as in Example 1 was repeated, except that in place of ethanol used in Example 1, a mixture of water (50% by weight) and isopropyl alcohol (50% by weight) was used. The results are shown in Table 4. The obtained filter exhibited high leukocyte removal efficiency and high platelet passage ratio. Specifically, the test for evaluating the blood filtering performance was conducted five times, and, in each run of the test, the platelet passage ratio was more than 80% (highest value: 92.0%; lowest value: 88.5%). Further, the hematocrit of the filtered blood was the same as that of the non-filtered blood. The amount of materials dissolved-out from the filter was substantially the same as that of materials dissolved-out from the filter substrate itself. An XPS analysis of a cross section of the filter showed that the filter substrate had a uniform coating of a polymer in the thickness-wise direction thereof.

EXAMPLE 9

Substantially the same procedure as in Example 1 was repeated, except that in place of human blood preserved for one day, freshly collected human whole blood was used (wherein, specifically, immediately after the collection of whole blood, CPD was added thereto, and then the whole blood was used 3 hours after the collection). The results are shown in Table 4. The obtained filter exhibited high leukocyte removal efficiency and high platelet passage ratio. Specifically, the test for evaluating the blood filtering performance was conducted five times, and, in each run of the test, the platelet passage ratio was more than 80% (highest value: 88.0%; lowest value: 83.5%). Further, the hematocrit of the filtered blood was the same as that of the non-filtered blood. The amount of materials dissolved-out from the filter was substantially the same as that of materials dissolved-out from the filter substrate itself. An XPS analysis of a cross section of the filter showed that the filter substrate had a uniform coating of a polymer in the thickness-wise direction thereof.

REFERENCE EXAMPLE 1

With respect to the hydrophilic copolymer used in Example 1, an acute toxicity test was performed. The results are shown in Table 5. The test showed that the hydrophilic copolymer had no problem in safety.

REFERENCE EXAMPLE 2

With respect to the crude hydrophilic copolymer (before purification) mentioned in Example 1, an acute toxicity test was performed. The results are shown in Table 5.

TABLE 1

|  | Example 1 | Example 2 | Comparative Example 1 | Comparative Example 2 | Comparative Example 3 |
|---|---|---|---|---|---|
| Leukocyte removal ratio (%) | 96.6 | 97.8 | 98.2 | 98.8 | 99.3 |
| Platelet passage ratio (%) | 90.4 | 82.1 | 72.8 | 28.0 | 19.5 |
| Amount of the polymer for coating (mg/m² (filter substrate)) | 115 | 60.0 | 16.6 | 5.0 | 1.8 |
| Coating ratio of the filter substrate (%) | 90 | 80 | 60 | 40 | 30 |

TABLE 2

|  | Example 3 | Example 4 | Example 5 | Example 6 | Example 7 |
|---|---|---|---|---|---|
| Leukocyte removal ratio (%) | 98.0 | 97.1 | 98.0 | 98.2 | 96.6 |
| Platelet passage ratio (%) | 87.9 | 84.3 | 81.4 | 81.9 | 83.1 |

TABLE 2-continued

|  | Example 3 | Example 4 | Example 5 | Example 6 | Example 7 |
|---|---|---|---|---|---|
| Amount of the polymer for coating (mg/m²(filter substrate)) | 116 | 113 | 17.2 | 17.4 | 17.2 |
| Coating ratio of the filter substrate (%) | 90 | 80 | 70 | 70 | 70 |

TABLE 3

|  | Comparative Example 4 | Comparative Example 5 | Comparative Example 6 | Comparative Example 7 | Comparative Example 8 |
|---|---|---|---|---|---|
| Leukocyte removal ratio (%) | 97.5 | 97.1 | 88.0 | 94.6 | 96.3 |
| Platelet passage ratio (%) | 73.0 | 71.1 | 86.2 | 68.7 | 20.5 |
| Amount of the polymer for coating (mg/m²(filter substrate)) | 16.2 | 16.0 | 15.5 | 16.8 | 4.8 |
| Coating ratio of the filter substrate (%) | 60 | 60 | 60 | 60 | 40 |

TABLE 4

|  | Example 8 | Example 9 |
|---|---|---|
| Leukocyte removal ratio (%) | 96.8 | 97.8 |
| Platelet passage ratio (%) | 90.0 | 85.2 |
| Amount of the polymer for coating (mg/m²(filter substrate)) | 112 | 115 |
| Coating ratio of the filter substrate (%) | 90 | 90 |

TABLE 5

|  | Reference Example 1 | Reference Example 2 |
|---|---|---|
| Number of mice tested | 10 | 10 |
| Average body weight (g) | 19.2 | 20.9 |
| Average dose (ml) | 0.96 | 1.04 |
| Observation period (number of days) | 5 | 5 |
| Results | Disorder or death of any mouse did not occurr. | 2 of the 10 mice exhibited some abnormal conditions (such as elevation of body temperature and an increase in spontaneous behavior). |

INDUSTRIAL APPLICABILITY

By the use of the filter of the present invention for selectively removing leukocytes, it becomes possible to efficiently remove leukocytes (which are causative of various side effects of a transfusion) from human whole blood while holding down a loss of the following 3 blood components: plasma, red cells and platelets. Therefore, the filter of the present invention is extremely useful for the production of blood products for use in the pharmaceutical industry, the medical industry and general industries.

What is claimed is:

1. A filter for selectively removing leukocytes from human whole blood, comprising a filter substrate having coated thereon a hydrophilic synthetic polymer in a coating ratio of 70% or more with respect to the overall surface of the filter substrate, said polymer containing a nonionic hydrophilic group and a nitrogen-containing basic functional group, and wherein said polymer having a weight average molecular weight of from 300,000 to 3,000,000.

2. The filter according to claim 1, wherein said hydrophilic synthetic polymer is a vinyl polymer.

3. The filter according to claim 1, wherein said filter substrate comprises a polymer containing a functional group having a lone electron pair.

4. The filter according to claim 1, wherein said filter substrate comprises a thermoplastic polymer.

5. The filter according to claim 1, wherein said filter substrate is a non-woven fabric.

6. The filter according to claim 1, wherein said filter substrate has been subjected to at least one treatment selected from the group consisting of energy beam irradiation treatment and electric discharge treatment.

7. The filter according to claim 1, wherein said hydrophilic synthetic polymer has a molecular weight distribution wherein, in a gel permeation chromatogram of said polymer, the content of low molecular weight fractions having molecular weights which are ¼ or less of the peak-top molecular weight is 10% or less in terms of the percentage of an area in the peak which corresponds to said low molecular weight fractions, based on the entire area of the peak.

8. A method for selectively removing leukocytes from human whole blood, comprising:
    contacting human whole blood with the filter of claim 1, thereby causing leukocytes contained in the human whole blood to selectively adhere to said filter while allowing plasma, red cells and platelets contained in the human whole blood to pass through said filter to obtain a leukocyte-removed blood suspension, and
    collecting said leukocyte-removed blood suspension.

9. The filter according to claim 2, wherein said filter substrate comprises a polymer containing a functional group having a lone electron pair.

10. The filter according to claim 2, wherein said filter substrate comprises a thermoplastic polymer.

11. The filter according to claim 2, wherein said filter substrate is a non-woven fabric.

12. The filter according to claim 2, wherein said filter substrate has been subjected to at least one treatment selected from the group consisting of energy beam irradiation treatment and electric discharge treatment.

13. The filter according to claim 2, wherein said hydrophilic synthetic polymer has a molecular weight distribution wherein, in a gel permeation chromatogram of said polymer, the content of low molecular weight fractions having molecular weights which are ¼ or less of the peak-top molecular weight is 10% or less in terms of the percentage of an area in the peak which corresponds to said low molecular weight fractions, based on the entire area of the peak.

14. A method for selectively removing leukocytes from human whole blood, comprising:
  contacting human whole blood with the filter of claim 2, thereby causing leukocytes contained in the human whole blood to selectively adhere to said filter while allowing plasma, red cells and platelets contained in the human whole blood to pass through said filter to obtain a leukocyte-removed blood suspension, and
  collecting said leukocyte-removed blood suspension.

* * * * *